US009541504B2

(12) United States Patent
Hoyt

(10) Patent No.: US 9,541,504 B2
(45) Date of Patent: Jan. 10, 2017

(54) ENHANCING VISUAL ASSESSMENT OF SAMPLES

(75) Inventor: Clifford C. Hoyt, Wellesley, MA (US)

(73) Assignee: Cambridge Research & Instrumentation, Inc., Hopkinton, MA (US)

( * ) Notice: Subject to any disclaimer, the term of this patent is extended or adjusted under 35 U.S.C. 154(b) by 309 days.

(21) Appl. No.: 13/204,173

(22) Filed: Aug. 5, 2011

(65) Prior Publication Data

US 2012/0112098 A1 May 10, 2012

Related U.S. Application Data

(60) Provisional application No. 61/371,151, filed on Aug. 5, 2010.

(51) Int. Cl.
| | | |
|---|---|---|
| G01N 21/00 | (2006.01) |
| G01N 21/64 | (2006.01) |
| B82Y 30/00 | (2011.01) |
| G01N 1/30 | (2006.01) |
| G06T 5/50 | (2006.01) |
| G06K 9/00 | (2006.01) |

(52) U.S. Cl.
CPC ........... *G01N 21/6458* (2013.01); *B82Y 30/00* (2013.01); *G01N 1/30* (2013.01); *G01N 21/6428* (2013.01); *G06K 9/0014* (2013.01); *G06T 5/50* (2013.01); *G01N 2021/6441* (2013.01); *G06T 2207/10056* (2013.01); *G06T 2207/10064* (2013.01); *G06T 2207/30024* (2013.01)

(58) Field of Classification Search
CPC .................................................. G01N 21/6456
USPC ....................................................... 436/172
See application file for complete search history.

(56) References Cited

U.S. PATENT DOCUMENTS

| | | | |
|---|---|---|---|
| 5,521,705 A | 5/1996 | Oldenbourg et al. |
| 5,539,517 A | 7/1996 | Cabib et al. |
| 5,784,162 A | 7/1998 | Cabib et al. |
| 5,859,700 A | 1/1999 | Yang |
| 5,991,028 A | 11/1999 | Cabib et al. |

(Continued)

FOREIGN PATENT DOCUMENTS

| | | | | |
|---|---|---|---|---|
| JP | S57-094052 | 6/1982 | ............. | C09B 67/00 |
| JP | H05-505876 | 8/1993 | ............. | G01N 21/76 |

(Continued)

OTHER PUBLICATIONS

L. Buchynska, E. Kashuba, L. Szekely, "Immunofluorescence Staining of Paraffin Sections: Creating DAB Staining Like Virtual Digital Images Using CMYK Color Conversion" Experimental Oncology 30, 327-329, 2008.*

(Continued)

*Primary Examiner* — Christopher A Hixson
*Assistant Examiner* — Emily Berkeley
(74) *Attorney, Agent, or Firm* — Fish & Richardson P.C.

(57) ABSTRACT

Methods and systems for imaging a biological sample are disclosed, and include: (a) staining the sample with a first stain that includes eosin and at least one additional stain; (b) directing excitation light to the sample to cause each of the stains to emit fluorescence; and (c) recording images of the fluorescence emitted from the stains in the sample, where the amount of eosin in the sample is sufficiently dilute to cause the sample to have an average optical density of less than 0.10 at green wavelengths.

34 Claims, 28 Drawing Sheets

(56) References Cited

U.S. PATENT DOCUMENTS

| | | | |
|---|---|---|---|
| 5,995,645 A | 11/1999 | Soenkson et al. | |
| 6,007,996 A | 12/1999 | McNamara et al. | |
| 6,142,629 A | 11/2000 | Adel et al. | |
| 6,195,451 B1 * | 2/2001 | Kerschmann | G06T 5/50 382/133 |
| 6,348,325 B1 | 2/2002 | Zahniser et al. | |
| 6,373,568 B1 | 4/2002 | Miller et al. | |
| 6,421,131 B1 | 7/2002 | Miller | |
| 6,690,466 B2 | 2/2004 | Miller et al. | |
| 6,920,239 B2 | 7/2005 | Douglass et al. | |
| 6,924,893 B2 | 8/2005 | Oldenbourg et al. | |
| 2003/0081204 A1 | 5/2003 | Cronin et al. | |
| 2003/0138140 A1 | 7/2003 | Marcelpoil et al. | |
| 2003/0223248 A1 | 12/2003 | Cronin et al. | |
| 2005/0065440 A1 | 3/2005 | Levenson | |
| 2006/0082762 A1 | 4/2006 | Leverette et al. | |
| 2006/0119865 A1 | 6/2006 | Hoyt et al. | |
| 2006/0245631 A1 | 11/2006 | Levenson et al. | |
| 2007/0016082 A1 | 1/2007 | Levenson et al. | |
| 2007/0231784 A1 | 10/2007 | Hoyt et al. | |
| 2008/0026366 A1 * | 1/2008 | Harkins | G01N 1/30 435/5 |
| 2008/0074644 A1 | 3/2008 | Levenson et al. | |
| 2008/0074649 A1 | 3/2008 | Levenson et al. | |
| 2008/0272312 A1 * | 11/2008 | Tuschel | 250/459.1 |
| 2009/0226059 A1 | 9/2009 | Levenson et al. | |
| 2009/0257640 A1 | 10/2009 | Gossage et al. | |
| 2010/0075373 A1 | 3/2010 | Hoyt | |
| 2011/0182490 A1 | 7/2011 | Hoyt et al. | |
| 2012/0224053 A1 * | 9/2012 | Vykoukal et al. | 348/135 |

FOREIGN PATENT DOCUMENTS

| | | | |
|---|---|---|---|
| JP | H06-100466 | 4/1994 | A61K 45/00 |
| JP | 2002-544531 | 12/2002 | G01N 33/48 |
| JP | 2003-504627 | 2/2003 | G01N 33/53 |
| JP | 2003-065948 | 3/2003 | G01N 21/27 |
| JP | 2004-532410 | 10/2004 | G01N 21/27 |
| WO | WO 91/15867 | 10/1991 | H01J 5/16 |
| WO | WO 98/43042 | 10/1998 | |
| WO | WO 00/70541 | 11/2000 | G06K 9/00 |
| WO | WO 01/04828 | 1/2001 | G06K 9/00 |
| WO | WO 02/086498 | 10/2002 | G01N 44/38 |
| WO | WO 2005/040769 | 5/2005 | |
| WO | WO 2006/081547 | 8/2006 | |
| WO | WO 2008/039758 | 4/2008 | |
| WO | WO 2009/068546 | 6/2009 | G01N 21/64 |
| WO | WO 2010/011953 | 1/2010 | G02B 21/26 |
| WO | WO 2010/056945 | 5/2010 | G01N 33/48 |
| WO | WO 2010056945 A2 * | 5/2010 | G01N 33/50 |

OTHER PUBLICATIONS

B. Badir, B. Knight, "Fluorescence Microscopy in the Detection of Early Myocardial Ingarction" Forensic Science International, 34, 99-102, 1987.*

Chemistry of the H&E Stain by Mickie Johnson ASMH 2009.*

C.Y Fu, U.S Dinish, B.K Ng, V.M Murukeshan, L.K Seah, and S.K Lim-Tan "Fluorescence Lifetime Imaging of Haematoxylin and Eosin-stained Cervical Tissue" Intl. Conf. on Biomedical and Pharmaceutical Engineering 2006 (ICBPE 2006) pp. 368-372.*

Kevin Francis Sullivan, Steve A. Kay "Green Fluorescent Proteins" Gulf Professional Publishing, 1999. Chapter 3 Piston et al.*

Examiner accessed Protocol via the site http://www.histology.to/eosin.html on Mar. 17, 2015.*

T. J. Porro, Sandra P. Dadik, Mark Green and Helen T. Morse "Fluorescence and Absorption Spectra of Biological Dyes" Stain Technology (1963), 38, pp. 37-48.* http://www.newcomersupply.com/products/special-stains?page=E#142 accessed by examiner on Nov. 30, 215.*

Notification Concerning Transmittal of International Preliminary Report on Patentability with regard to International Application No. PCT/US2011/046808 dated Feb. 14, 2013 (8 pages).

Badir et al., "Fluorescence Microscopy in the Detection of Early Myocardial Infarction," *Forensic Science International* 34: 99-102 (1987).

Search Report and Written Opinion in PCT Patent Application No. PCT/US2011/046808, dated Nov. 8, 2011.

Badir et al., "Fluorescence microscopy in the detection of early myocardial infarction," *Forensic Science International*, vol. 34(1-2); pp. 99-102 (1987).

International Search Report and Written Opinion for International Application No. PCT/US2011/046808, dated Nov. 8, 2011.

Japanese Office Action from the Japanese Patent Office for Japanese Application No. 2013-523368 dated Oct. 6, 2014 (8 pages).

Japanese Office Action for Japanese Application No. 2013-523368 dated May 1, 2015 (5 pages).

Summer L. Gibbs et al., "Near-Infrared Fluorescent Digital Pathology for the Automation of Disease Diagnosis and Biomarker Assessment", *Molecular Imaging*, pp. 1-9 (2015).

Examiner's Report issued by the Canadian Patent Office for Canadian Patent Application No. 2806621 by Examiner Tariq Khader dated Jun. 15, 2016 (2 pages).

* cited by examiner

ENHANCING VISUAL ASSESSMENT OF SAMPLES

CROSS-REFERENCE TO RELATED APPLICATIONS

This application claims priority to U.S. Provisional Patent Application No. 61/371,151, filed on Aug. 5, 2010, the entire contents of which are incorporated herein by reference.

TECHNICAL FIELD

This disclosure relates to staining, visualization, and analysis of biological samples including cells and tissue.

BACKGROUND

Analysis of cells and tissue samples can involve preparing the sample with stains, including histological stains or immunofluorescent (IF) probes, and then determining the amount of stain present at various locations in the sample.

Automated image analysis of such samples can include finding areas of interest within tissue samples, locating certain types of cells, and/or locating sub-cellular compartments within cells of interest, and determining the amount of stain in various regions, cells and/or sub-cellular compartments. Little or no user intervention is required in many cases.

IF probes have molecular specificity so they bind only to regions of a sample where a target compound is present, and the amount of probe binding is approximately proportional to the amount of the target compound present. Because multiple IF probes can be applied to a single sample, it is possible to measure several analytes in a given cell or tissue section.

A common way to prepare cell or tissue samples for visual review or automated image analysis is via hematoxylin and eosin (H&E) staining protocols that produce vivid color contrast when the sample is viewed in a transmitted-light microscope.

SUMMARY

In general, in a first aspect, the disclosure features methods for imaging a biological sample that include: (a) staining the sample with a first stain that includes eosin and at least one additional stain; (b) directing excitation light to the sample to cause each of the stains to emit fluorescence; and (c) recording images of the fluorescence emitted from the stains in the sample, where the amount of eosin in the sample is sufficiently dilute to cause the sample to have an average optical density of less than 0.10 at green wavelengths.

Embodiments of the methods can include any one or more of the following features.

The amount of eosin in the sample can be sufficiently dilute to cause the sample to have an average optical density of less than 0.05 at green wavelengths. The green wavelengths can be 530 nm through 570 nm.

Staining of the sample with the first stain including eosin can include contacting the sample for one second or less with a solution having an eosin concentration of 0.01 g or less of eosin per 100 mL of solution.

The amount of eosin in the sample can be sufficient to produce detectable fluorescence by the eosin in response to the excitation light. The eosin can include at least one of eosin Y, eosin B, and phloxine.

The recorded images can be spectrally resolved into different spectral bands. At least some of the spectral bands can correspond to a fluorescence wavelength range for a respective one of the stains.

The biological sample can include blood, cells, or tissue sections.

The at least one additional stain can include a fluorescent nuclear counterstain. The fluorescent counterstain can include DAPI or Hoechst. The at least one additional stain can include at least one immunofluorescent stain. The immunofluorescent stain can include quantum dots.

Directing the excitation light can include sequentially directing excitation light in different spectral bands to the sample. Recording the fluorescence can include recording images of the fluorescence in each of multiple different spectral bands.

The method can include computationally processing the recorded images to obtain information about the sample. Processing the recorded images can include spectrally unmixing the recorded images into unmixed images, where each unmixed image corresponds to fluorescence from a respective one of the stains. Processing the recorded images can include generating a bright-field image of the sample from the recorded fluorescence images. The bright-field image can include pink regions corresponding regions of the sample that localize eosin and blue regions corresponding to regions of the sample containing nuclei. The bright-field image can include additional regions rendered to correspond to regions of the sample that localize an immunofluorescent stain.

The method can include outputting the information about the sample. The outputted information can include a synthetic image derived from the recorded images.

A difference between the average optical density of the sample in the green wavelengths and an average optical density of the sample at red wavelengths can be 0.08 or less. The red wavelengths can be 610 nm through 650 nm.

The contribution of the eosin to the average optical density of the sample can be less than 0.05.

Embodiments of the methods can also include any of the other features disclosed herein, in any combination, as appropriate.

In another aspect, the disclosure features methods for imaging a biological sample that include: (a) staining the sample with a first stain that includes eosin, a nuclear counterstain, and at least one immunofluorescent stain, where the amount of eosin in the sample is sufficiently dilute to cause the sample to have an average optical density of less than 0.10 at green wavelengths; (b) directing excitation light to the sample to cause each of the stains to emit fluorescence, where the amount of eosin in the sample is sufficient to produce detectable fluorescence by the eosin in response to the excitation light; (c) recording images of the fluorescence emitted from the stains in the sample; (d) computationally processing the recorded images to produce a synthetic image; and (e) displaying the synthetic image.

Embodiments of the methods can include any one or more of the following features.

The synthetic image can include a bright-field image that features pink regions corresponding regions of the sample that localize eosin, blue regions corresponding to regions of the sample containing nuclei, and additional regions rendered to correspond to regions of the sample that localize the immunofluorescent stain.

Processing the recorded images can include spectrally unmixing the recorded images into unmixed images, where each unmixed image corresponds to fluorescence from a respective one of the stains.

The biological sample can include blood.

The eosin in the sample can have an average optical density of less than 0.05 at wavelengths between 530 nm and 580 nm. A difference between the average optical density of the sample at the green wavelengths and an average optical density of the sample at red wavelengths can be 0.08 or less. The red wavelengths can be 610 nm through 650 nm.

The contribution of the eosin to the average optical density of the sample can be less than 0.05.

Embodiments of the methods can also include any of the other features disclosed herein, in any combination, as appropriate.

In a further aspect, the disclosure features methods for imaging a biological sample that include: (a) staining the sample with a first stain that includes eosin and at least one additional stain; (b) directing excitation light to the sample to cause each of the stains to emit fluorescence; and (c) recording images of the fluorescence emitted from the stains in the sample, wherein the amount of eosin in the sample is less than that used for conventional bright-field H&E staining.

Embodiments of the methods can include any of the other features disclosed herein, in any combination, as appropriate.

Unless otherwise defined, all technical and scientific terms used herein have the same meaning as commonly understood by one of ordinary skill in the art to which this disclosure belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and description below. Other features and advantages will be apparent from the description, drawings, and claims.

DESCRIPTION OF DRAWINGS

Like reference symbols in the various drawings indicate like elements.

DETAILED DESCRIPTION

Figure 1:
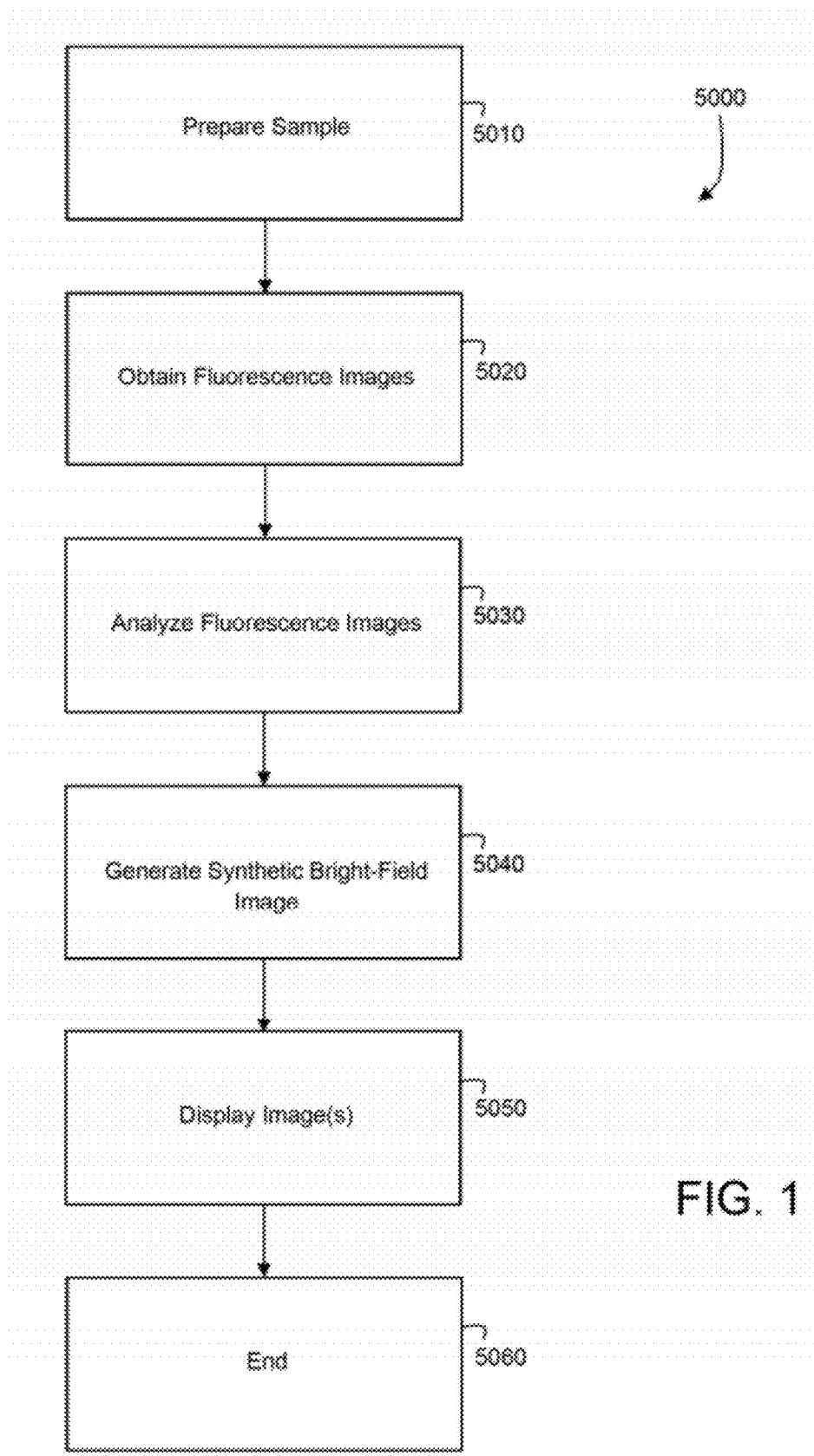
FIG. 1 is a flow chart showing a series of steps in a method for sample assessment.

Eosin is a stain that is commonly applied to cells and tissues as part of a hematoxylin and eosin preparation to generate brightfield images of the samples. As used herein, a stain is any composition that when applied to a biological sample produces an optically detectable signature sufficient to spatially identify where the composition is localized in the sample, and a brightfield image of a sample is an image that corresponds to a view of light transmitted through the sample. Visual color and contrast are produced by the mechanism of light absorption and/or scattering when light propagating through the sample encounters stains such as eosin.

The methods and systems disclosed herein can be used in fluorescence imaging of samples, where the light that forms an image at a detector (or in the eye of an operator) corresponds to fluorescence emission from the sample. To obtain fluorescence images, a sample is typically exposed to incident light in a certain wavelength band which excites molecules in the sample. The excited molecules emit fluorescent light at a different, longer wavelength, and the emitted light is detected and used to form one or more sample images. Multiple excitation and emission bands can be used, and it is possible to image several different molecular species, for example, by detecting emission in different wavelength bands. A fluorescence image is an example of a "dark-field image" because the fluorescence emitted from the sample is viewed against a dark background.

The systems and methods disclosed herein can be applied to fluorescence imaging of biological samples, for example. In particular, the methods and systems can be used to stain biological samples—which can also contain other fluorescent compounds—with eosin. As used herein, a biological sample is a sample that includes material extracted from an animal (including a human) such as blood, cells, and/or tissue. Moreover, as used herein, fluorescence is the visible or invisible radiation emitted by a substance in response to incident radiation of a shorter wavelength.

The methods and systems disclosed herein are typically used to apply dilute amounts of eosin to samples that are also prepared using immunofluorescent (IF) labeling, and are then imaged using fluorescent imaging techniques. As used herein, an immunofluorescent stain is a stain that is selective for a specific antigen or antibody in the biological sample and exhibits fluorescence. In some embodiments, IF labeling utilizes quantum dots instead of, or in addition to, other fluorescent compounds or structures.

In some embodiments, samples are prepared with dilute amounts of eosin and with a fluorescent nuclear counterstain, and are then imaged using fluorescence imaging techniques. A synthetic H&E view of a sample can be produced based on the separate fluorescence signals corresponding to eosin and to the nuclear counterstain obtained from one or more images of the sample. The synthetic image is created such that the sample in the synthetic image appears to an observer as it would if it were stained according to a conventional H&E protocol and viewed in a transmitted-light microscope. The synthetic image can be presented to a researcher or clinician for analysis or for confirmation of an automated sample classification.

In certain embodiments, samples are prepared with dilute amounts of eosin, with a nuclear counterstain, and with IF labeling. Fluorescence imaging of a sample yields fluorescence emission signals corresponding to the eosin and to the nuclear counterstain as component images of the sample; these component images can be presented to an automated classifier, or used to generate synthetic H&E images of the sample for presentation to a clinician or researcher. One or more images corresponding to fluorescence emission from the IF label in the sample can provide further information about the sample, such as the presence or distribution of the compound targeted by the IF label.

Thus, for example, the methods and systems disclosed herein provide for visualization of a sample based on fluorescence emissions from the sample. The systems and methods also permit improved automated image analysis based on fluorescence emission signals, and for visual review and automated image analysis of the individual samples based on fluorescence emissions.

In some embodiments, the methods and systems disclosed herein can be used to locate and identify rare-event cells such as circulating tumor cells by fluorescence imaging. Cells that are examined to identify these events are very weakly stained with eosin after first applying a nuclear counterstain and/or one or more IF labels. Images corresponding to fluorescence emission from eosin and at least one other fluorescent entity are acquired, and these images can be used for improved automated classification or to create synthetic H&E views of the cells for visual assessment by a clinician or researcher.

The identification of cell nuclei and nuclear regions in cells and tissue samples is frequently of importance for purposes of sample classification and for diagnosis of conditions which affect the nuclear regions of cells. To identify nuclear regions, samples can be prepared using fluorescent compounds such as Hoechst and/or DAPI which preferentially bind to the nucleus within cells. Fluorescence emission from such compounds can be used to identify nuclear regions of interest.

Further, a wide variety of different IF labels can be used to identify particular proteins, nucleic acids, and other chemical moieties and/or structural entities in samples. The combination of information derived from the distribution of these IF labels within samples, and of the nuclear information provided by fluorescent nuclear stains, enables automated classification and assessment of stained tissue samples.

Classification and assessment of cells and tissue samples can be improved by providing additional structural information through the application of eosin to the samples, which preferentially binds to cytoplasm and certain other structures. This provides information about the samples that can be used for classification purposes and for visual assessment. Eosin is generally used in combination with chromogenic stains—most prominently with hematoxylin—using protocols designed for viewing stained samples by observing light transmitted through the samples. In transmitted-light imaging geometries, eosin appears as a vivid pink color, even in thin (e.g., 4 micron) tissue sections, because it strongly absorbs green light. As a result, eosin is readily detected by the human eye or by a detector such as a CCD camera.

In many situations, however, fluorescence imaging yields results that are more useful than transmitted-light imaging. For example, fluorescence imaging permits the use of more probes in a particular sample (e.g., a "multiplexing" advantage) so that a greater number of proteins, nucleic acids, and/or other moieties can be measured. Alternatively or in addition, for example, fluorescence imaging may yield more accurate quantitative results for measureable parameters such as concentrations of particular constituents within samples. In certain embodiments, advantageous fluorescent labeling protocols may already be established for particular assays of interest.

Experiments have revealed that when a sample is prepared according to a conventional eosin protocol and one or more fluorescent stains or IF labels are also applied to the sample, it is difficult to obtain high quality images corresponding to fluorescence emission from other applied stains or markers. In particular, eosin—when applied according to conventional staining protocols—interferes with fluorescence emission from other stains applied to the sample. Without wishing to be bound by theory, it is believed that this interference arises from quenching of fluorescence emission from the other stains by eosin, by independent fluorescence emission from eosin, or from a combination of these factors. As a result, sample images are generally difficult to analyze accurately, as signal attributable to eosin tends to dominate and obscure contributions from the other fluorescent stains and IF labels. Visual review based on such images is unsatisfying to clinicians and researchers.

General Methodology

In general, conventional eosin staining protocols are designed to apply significant amounts of eosin to samples to permit sensitive detection and quantitative measurement of compounds and structures to which eosin binds. As used herein, "conventional bright-field H&E imaging" refers to a process of staining a biological sample with hematoxylin and eosin to produce a bright-field image of the sample for visual inspection by a pathologist. The amount of eosin used is sufficiently large to absorb light in the green region of the electromagnetic spectrum and produce an image in which eosin-stained regions appear pink. As explained above, while the use of such quantities of eosin has been observed to yield accurate quantitative measurements, the applied eosin interferes with fluorescence emission from other stains and/or IF markers that may be present. It has been discovered, however, that eosin can be used successfully in combination with fluorescent nuclear stains and IF markers if the amount of eosin applied to samples is reduced greatly compared to the amount of eosin applied in standard chromogenic staining protocols. Surprisingly, even though the amount of eosin is reduced substantially, the spatial and quantitative accuracy of measurements associated with the eosin component are not affected. Moreover, measurements of contributions from fluorescent stains and/or IF labels can be performed without the significant confounding effects that would otherwise be present if eosin were applied in larger amounts.

Figure 2A:
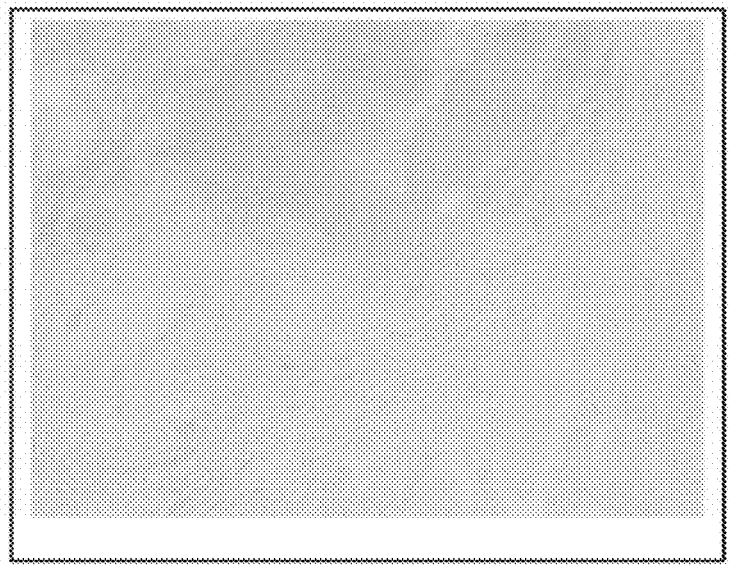
FIG. 2A is a transmitted-light image of a sample prepared with DAPI and an IF label consisting of a fluorochrome stain (ALEXA FLUOR® 594) conjugated to Her2.
Figure 2B:
FIG. 2B is a transmitted-light image of a sample prepared with DAPI and an IF label based on a fluorochrome stain (ALEXA FLUOR® 594) as in FIG. 2A, and further prepared according to a dilute eosin staining protocol of 0.0011% eosin Y and 0.00011% phloxine B for a period of 20 seconds.
Figure 2C:
FIG. 2C is a transmitted-light image of a sample prepared with DAPI and an IF label based on a fluorochrome stain (ALEXA FLUOR® 594) as in FIG. 2A, and further prepared according to a conventional eosin staining protocol of 0.112% eosin Y and 0.0112% phloxine B for a period of 20 seconds.

Typical eosin staining protocols for transmitted-light imaging expose a tissue sample to a solution having 0.12%-1.0% concentration of eosin Y by weight for a period of between 20 to 120 seconds. Some protocols also include 0.01% phloxine B by weight. Less commonly, eosin B is used in addition to, or instead of, eosin Y. After this treatment, sample regions where eosin is absorbed appear strongly colored to the human eye upon visual inspection. FIG. 2C shows an image of a breast tissue sample stained with a combination of DAPI and an IF label based on a fluorochrome stain (ALEXA FLUOR® 594), and further with a conventional eosin preparation consisting of 0.112% eosin Y by weight and 0.0112% phloxine B by weight for a period of 20 seconds, viewed in a transmitted-light imaging modality.

In contrast, the methods and systems disclosed herein for fluorescence imaging include the application of much smaller quantities of eosin to samples. In some embodiments, for example, a sample is exposed to an eosin solution that is less concentrated by a factor of about 20 than the eosin used in the conventional protocol just described (e.g., 0.005% eosin by weight), less concentrated by a factor of about 50 (e.g., 0.002% eosin by weight), less concentrated by a factor of about 100 (e.g., 0.001% by weight), or even less concentrated. Phloxine B is typically present at approximately 0.0005% concentration by weight or less (e.g., approximately 0.0002% by weight, approximately 0.0001% by weight).

The time that the sample is exposed to the eosin solution can generally vary. Typically, for example, the sample is exposed for a period of between one second and three seconds (e.g., for 3.0 s or less, 2.5 s or less, 2.0 s or less, 1.5 s or less, 1.0 s or less). In general, by reducing the concentration of the eosin staining solution and/or the exposure time of the sample, a smaller amount of eosin is applied to the sample.

Although the amount of eosin applied to the sample is significantly less than under conventional staining protocols, the distribution of eosin within cells and tissue continues to have specificity. It does not form a uniform, faint wash, but instead continues to selectively localize, and despite the shorter application time and lower concentration, the eosin preferentially localizes in the same structures as when conventional protocols are used.

When applied in this fashion, light absorption by eosin is significantly attenuated due to its relatively low concentration in samples. In general, light absorption by eosin in not readily observed by eye upon sample inspection. Thus, the presence of eosin is not visible, or only weakly visible, in transmitted-light microscope images. FIG. 2B shows an exemplary image of a sample prepared according to a dilute eosin staining protocol that included applications of DAPI and an IF label based on a fluorochrome stain (ALEXA FLUOR® 594), and a solution of 0.0011% eosin Y and 0.00011% phloxine B for 20 seconds. While certain sample structures are visible in FIG. 2B, the presence of eosin is generally not discernible and it makes only a minor contribution to the overall appearance of the sample. For purposes of comparison, a transmitted-light image of a tissue sample with no eosin is shown in FIG. 2A.

Figure 3A:
FIGS. 3A, 3B, and 3C are fluorescence emission images of the sample of FIG. 2B in blue, green, and red regions of the electromagnetic spectrum, respectively.

In spite of the relatively low concentration of eosin, measurement of fluorescence emission from samples stained according to the dilute eosin protocols disclosed herein readily reveals the presence and distribution of eosin. FIG. 3A shows an exemplary image of fluorescence emission in the green region of the electromagnetic spectrum from the same sample shown in FIG. 2A. The use of relatively sensitive fluorescence detection techniques permits a wide variety of different dilute eosin staining protocols to be used with samples according to the various aspects disclosed above.

In fluorescence imaging, eosin can typically be detected in the same general manner in which emission from other fluorescent compounds is detected. Eosin fluoresces when it is excited by blue light, and the color of the fluorescence emission is green to yellow. Thus the appearance of eosin in a fluorescent image is different from the pink appearance it has in a brightfield image. However, whether detected in transmitted light based on its absorption of incident light, or based on its fluorescence emission, eosin binds to the same sample structures. Thus, detection of either eosin absorption or fluorescence provides substantially the same structural information about the sample.

As discussed above, in addition to eosin, one or more fluorescent nuclear counterstains can be applied to a tissue sample prior to analysis. As used herein, nuclear counterstains are compounds that bind preferentially to structures within cellular nuclei. Exemplary fluorescent nuclear counterstains include Hoechst 33258, Hoechst 33342, and 4',6-diamidino-2-phenylindole (DAPI). Methods for preparing tissue samples with nuclear counterstains are disclosed, for example, in the document "DAPI Nucleic Acid Stain," available at internet address http://www.invitrogen.com/site/us/en/home/References/protocols/cell-and-tissue-analysis/dapi-protocol/dapi-nucleic-acid-stain.html. The entire contents of this document are incorporated herein by reference.

Further, as discussed above, one or more additional fluorescent markers can be applied to the sample to provide additional information about structural elements or biochemical moieties within the sample. In addition to IF probes that incorporate organic compounds that fluoresce, IF fluorescent markers can include quantum dot-based probes. These probes can be selected according to their spectral properties (e.g., emission wavelengths) and in general, multiple different probes that selectively bind to different types of structures or to different compounds can be applied to a sample.

In some embodiments, the markers can be selected such that all can be excited using relatively narrowband incident radiation. Inducing fluorescence emission from each of the stains and markers can therefore be accomplished with excitation radiation from a common source, and the fluorescence from each of the stains and markers can be separately measured to yield a wide variety of information about the sample. For example, a sample can be prepared using dilute eosin, with DAPI at 20,000:1 dilution, and using IF labels based on quantum dots that emit at 605 nm. The sample can then be excited using a source of ultra-violet (UV) light in the range 340-400 nm. A long-pass filter in the imaging system can be used to permit transmission of light only in the range from 430 nm to 680 nm, and to block UV light. Fluorescent emission from all species (e.g., eosin, DAPI, and the IF labels) can then be observed in a single fluorescence image of the sample.

In some embodiments, markers that are excited at different wavelengths can be applied to samples. Multi-band filters can be used to filter light from a broadband excitation source to produce a light beam with energy in multiple wavelength bands, and fluorescence emission from all markers applied to the sample can be imaged at the same time. Alternatively, in certain embodiments, single-band filters can be used in succession, and fluorescence emission from each of the applied markers can be measured sequentially. Techniques for multiple-wavelength excitation and fluorescence emission detection are known in the art of fluorescence microscopy.

When sample staining is complete, the stained sample can be imaged and assessed using a variety of semi-automated and fully automated methods. FIG. 1 shows a flow chart 5000 that features a series of steps for performing an assessment of a sample. The first step 5010 in flow chart 5000 is to prepare the sample. As discussed above, preparation of the sample includes applying eosin, a nuclear counterstain, and—optionally—one or more additional fluorescent stains or IF probes to the sample.

Once prepared, the sample is exposed to incident light in step 5020 and the fluorescence emission from the sample is measured (e.g., by obtaining one or more fluorescence images of the sample). In particular, a single fluorescence image of the sample can be obtained using a spectrally-sensitive detector such as a color camera. Alternatively, a series of fluorescence images of the sample can be obtained by using a series of optical filters that correspond to emission wavelengths for the various stains applied to the sample. In some embodiments, a spectral cube of sample images can be obtained, in which each plane of the cube corresponds to a sample image at a particular fluorescence wavelength; planes in the cube can be obtained while the sample is excited by light in one or more spectral bands.

In step 5030, the images are analyzed to obtain component images corresponding to each stain component present in the sample. Ideally, each component image corresponds primarily to the contribution from a single fluorescent component in the sample. For example, images of samples prepared as disclosed herein can be analyzed to yield a component image corresponding to eosin, a component image corresponding to each of the applied nuclear stains, and component images corresponding to each of the additional fluorescent stains and immunofluorescent markers. Images of samples can also be analyzed to yield one or more autofluorescence components images.

In some embodiments, the analysis can include assigning a particular image or color plane to a sample component. For example, a sample prepared with DAPI, dilute eosin, and an IF label (e.g., an IF label based on a fluorochrome stain such as ALEXA FLUOR® 594) can be imaged using a triple-band filter (available, for example, as Filter No. 69002 from Chroma Technology Corp., Bellows Falls, Vt.). The blue signal in the resulting color fluorescence image can be assigned to DAPI fluorescence, the green signal can be assigned to eosin fluorescence, and the red signal can be assigned to fluorescence from the IF label (e.g., ALEXA FLUOR® 594). This approach has the benefit of simplicity, and can be used where the number of component sought is relatively low (e.g., 3 or less), and background autofluorescence is low.

In certain embodiments, the sample can be imaged using several filters in sequence. This technique can yield improved component images if suitable wavelength ranges of light that preferentially excite one component and not the others can be identified. For example, to image the sample described above using a series of excitation filters, a first image can be obtained while the sample is excited with light centered at 350 nm and viewed with a bandpass filter that transmits light in the 435-480 nm range (Filter No. 49000, available from Chroma Technologies Corp.). A second image can be obtained while the sample is excited with light centered at 500 nm, and viewed with a longpass filter that transmits light in the 520-700 nm range (Filter No. 49029, available from Chroma Technologies Corp.). A third image can be obtained while the sample is excited with light in the 530-560 nm range, and viewed with a filter that transmits light in the 570-640 nm range (Filter No. 49006, available from Chroma Technologies Corp.). In this example, the analysis consists of assigning the first image as the component image corresponding to DAPI fluorescence, the second image as the component image corresponding to eosin fluorescence, and the third image as the component image corresponding to fluorescence from a fluorochrome stain (ALEXA FLUOR® 594).

In some embodiments, a spectral image cube can be obtained by measuring fluorescence emission from the sample using one or more filter sets, and the analysis includes unmixing the image cube to generate component images corresponding to the different fluorescence signals of the components. Methods for spectral imaging of samples and unmixing of spectral images are generally disclosed, for example, in commonly owned U.S. Pat. Nos. 7,555,155 and 7,321,791 and U.S. Patent Application Publication No. US 2008/0294032, the entire contents of each of which are incorporated herein by reference. When spectral unmixing techniques are employed, the unmixing computation can include reference spectral data associated with autofluorescence in the sample as a way to isolate autofluorescence contribution from the fluorescence emission signals of the markers and stains applied to the sample.

In optional step 5040, a synthetic brightfield image of the sample can be generated. To generate the synthetic brightfield image, the component images corresponding to one or more of the applied stains and markers are converted into a synthetic component absorption images. In the fluorescence component images, the signal at each pixel corresponds to the fluorescence intensity at that pixel. The fluorescence intensity information is used to convert the fluorescence emission component image into a component absorption image in which the intensity at each pixel is related to the absorption of incident light by the components of the sample at that pixel. Each component in the synthetic image can be assigned a target color that can be freely selected, e.g., to highlight certain structural features of the sample, to show the distribution of particular components in the sample, and/or to produce synthetic absorption images that resemble the images that would be obtained by direct measurement of sample absorption. That is, by using appropriately selected target colors and component images, synthetic absorption images of the sample can be rendered, and the synthetic images correspond to the image of the sample that would be observed if absorptive stains with the desired target colors were viewed in a transmitted light microscope. As an example, synthetic absorption images of a sample stained with a nuclear counterstain and eosin can be created, where the target color for rendering the nuclear counterstain is a blue color, and the target color for rendering eosin is a pink color. These colors are selected because they are associated with hematoxylin and eosin in a sample prepared using a conventional H&E preparation and viewed in a transmitted light microscope. More generally, other colors can be chosen for a variety of purposes, including improved acuity in the image.

In addition to synthetic H&E views, the appearance of a single component (or more than one component) in the sample can be rendered to view it in isolation. In general, the number of components shown in the synthetic view need not match the number of actual components in the sample. When several fluorescent components are present in the sample, a variety of useful combinations of fluorescence contributions from sample components can be rendered as sample images. For example, a sample image can be created that includes contributions from a nuclear counterstain and from an IF probe, to simulate a transmitted-light image of immunohistochemical (IHC) staining of hematoxylin and DAB. In some embodiments, fluorescence component images of the sample can be rendered as individual component bright-field images.

Absorption images can be calculated, for example, where color at each pixel is represented as a triplet of red, green, blue (RGB) values, which may be preferred for many applications. Colors can also be represented in other color spaces, however, such as the hue-saturation-intensity color space. In some embodiments, colors can be represented using a spectrum where individual entries correspond to specific wavelengths. These different methods of representing colors are well known in the fields of colorimetry and computer graphics.

Figure 11:
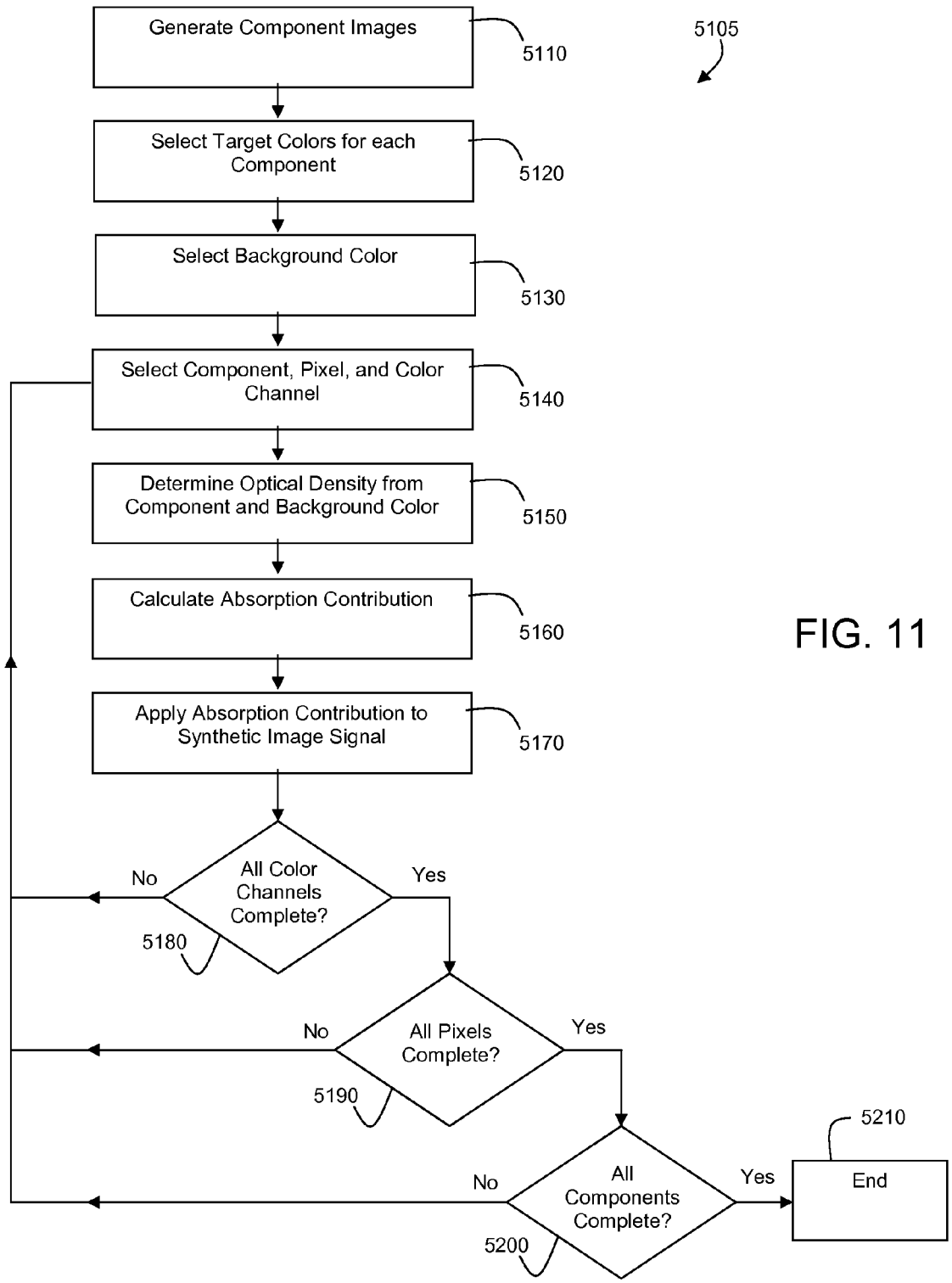
FIG. 11 is a flow chart that includes a series of steps for preparing a synthetic transmitted-light image of a sample from fluorescence emission signals for the sample.

FIG. 11 shows a flow chart 5105 that includes a series of steps for constructing an absorption image of the sample. In a first step 5110, suitable component images are selected, as will be discussed in greater detail below. Typically, the component images correspond to spectral contributions from individual components within the sample (e.g., stains and/or markers applied to the sample, and autofluorescence).

Next, in step 5120, target colors are selected for each component. The colors can be selected to mimic the colors that would be observed by an operator viewing an image of the sample, or they can be selected to highlight certain features of the sample, such as the localization of one or more of the applied stains. For example, to generate a synthetic bright-field image of the sample from fluorescence component images, the selected eosin component target color can be pink, and the selected DAPI component target color can be blue, as these are the colors in which eosin and DAPI appear in transmitted light H&E images.

In step 5130, an initial background color value is chosen. The background color defines an initial amount of red, green, and blue signal at each pixel, and it is the color that appears in regions of the image where no sample is present. The background color is usually white, meaning equal amounts of each primary color, but it need not be. Then, at each pixel, the amount of a particular color signal (e.g., red) is attenuated by an amount that depends on the signal value in the corresponding pixel of the first selected component image, and the target color for that component. This simulates the absorption of light by a stain having the target color, with the amount of stain represented by the signal in the component image.

Next, the synthetic image is created pixel-by-pixel. Within each image pixel, contributions from all components are calculated, and for each component, contributions in all color channels are determined. The process begins in step 5140 where a pixel location, component, and color channel are selected.

The well-known Beer-Lambert law states that the intensity of light passing through an absorptive material is given by $I=I_0 \cdot 10^{-OD}$, where the intensity of light I decreases from an initial value $I_0$ due to absorption according to exponential decay, which is conventionally described in units of optical density, or OD. The degree of absorption generally depends on wavelength. This notation can be used to describe the measured absorption in a real physical sample, or to describe simulated absorption, such as when generating a synthetic image as described herein.

To calculate the amount of a particular color at a given pixel, one can assign an optical density for that color of light that is proportional to the measured fluorescence signal at the pixel (which indicates the amount of stain that is present) and is further proportional to a characteristic absorption factor K that is associated with the target display color of the component associated with the color. For example, in the red channel at a given pixel, the optical density of the red color signal, OD (Red), can be calculated as $$OD(Red)=K_{red}*C$$

where C is the component signal strength and $K_{red}$ is the absorption factor for the component. This calculation is performed in step 5150 to determine the optical density associated with a particular color channel (e.g., red).

Then, in step 5160, the resulting color channel signal (e.g., red) is calculated as $I_{Red}=I_0 \cdot 10^{-OD(Red)}$, where $I_0$ is the background red value. This calculation is performed for red, green, and blue color channels, or, in other color spaces, for each spectral channel in the color space.

In some embodiments, the proportionality factor K between fluorescent signal strength and the amount of absorption can vary for different color channels depending on the target color. For example, to produce a blue target color, higher K values are typically assigned to the green and red channels than to the blue channel for a given fluorescent signal strength. In general, therefore, the values for $K_{red}$, $K_{green}$ and $K_{blue}$ may all be different from one another, or some (or all) of the values may be equal.

Next, in step 5170, the calculated absorbance is applied to the selected color channel (e.g., red) to represent the absorptive contribution of the selected component in that color channel to the synthetic image.

The same process is performed for all color channels and pixels in the image, as shown in steps 5180 and 5190 of flow chart 5105. The result is a simulated transmitted-light image of that component, as it would appear against a background of the chosen color if it were an absorptive stain having the selected target color.

The image is then further processed to simulate the effects of other components present in the sample, as desired, as shown in step 5200 of flow chart 5105. For each additional component, the red signal at each pixel is further attenuated by an amount that depends on the signal value in that component image, and the target color for that component. This is repeated for the green and blue channels, and the same process is performed for all pixels in the image. The result is an image that represents the appearance of a sample having the selected components, if each component were an absorptive stain having its requested target color, and if the sample was viewed in transmitted light against a background of the chosen background color.

When all color channels, pixels, and components have been processed, the procedure shown in flow chart 5105 terminates at step 5210.

For computational efficiency, it is useful to calculate the absorption factors for each target color ahead of time, at a variety of component signal strengths, and save these in look-up tables (LUTs). Then, for each component being rendered, the component signal strength at a given pixel can be used to choose an entry from the corresponding LUT which contains the color-wise absorption values for that component. The absorption values for all components are then multiplied with the background color to yield the resultant color at a given pixel. Look-up tables generally include a series of elements (e.g., 256 elements); individual elements $LUT_i$ in a look-up table can be calculated as:

$$LUT_i=\{(Tr/255)^{i/255}, (Tg/255)^{i/255}, (Tb/255)^{i/255}\}$$

where $LUT_i$ is the i-th entry in the table (e.g., a 256-element table), and Tr, Tg, and Tb are the RGB values of the target color, with colors are represented on a 0-255 scale with white equal to {255, 255, 255}.

The process generates a synthetic brightfield image of the sample, where the intensity at each pixel in the image corresponds to the amount of light "transmitted" through the sample (e.g., the amount of light not absorbed by any of the sample's absorptive components). This image can be displayed to a system operator, for example, as indicated in optional step 5050, and/or stored for further processing.

In step 5040, a simulated hematoxylin & eosin (H&E) image of the sample can be generated. This can be done using the synthetic brightfield calculation methods just described, based on nuclear counterstain and eosin component images, with target colors of blue and pink, respectively. Simulated H&E images can be useful because they can be displayed to a system operator, who can be a clinician, pathologist, or researcher. Such persons are trained to recognize disease states and tissue structures in H&E images, and this type of imagery is often most commonly used in laboratory clinical analysis. By recognizing the unique role of H&E imagery in clinical and research practice, the systems and methods herein provide uniquely useful data that help the operator confirm that image segmentations and object classifications were accurately performed. As a result, clinicians, researchers, and pathologists can play an important quality control function in otherwise automated assessment of tissue samples. Overall, the methods and systems disclosed herein permit the use of fluorescent stains and markers to generate synthetic H&E-like images to assist human operators to identify tissue architectures and disease states, while at the same time collecting specific molecular information based on IF marker localization.

Alternatively, or in addition, other images can also be displayed at step 5050, including one or more of the components images, either as a fluorescent images or a brightfield images. Moreover, such images can be displayed separately on different regions of a common screen or on different screens, and/or they can be overlaid with one another and displayed. A user interface permits the user to select between different display options. The overall process then terminates at step 5060.

The amount of eosin used in dilute eosin staining protocols is typically selected to yield images with a particular average optical density over a range of wavelengths. As used herein, an average optical density over a range of wavelengths is equal to an integral or summation of the wavelength-dependent optical density over the wavelength range divided by the width of the wavelength range. In some embodiments, for example, the amount of eosin in the sample is sufficiently dilute to cause the sample to have an average optical density of less than 0.10 at green wavelengths (e.g., less than 0.08 at green wavelengths, less than 0.06 at green wavelengths, less than 0.05 at green wavelengths, less than 0.03 at green wavelengths). Green wavelengths can include wavelengths in a range from 530-570 nm, for example.

In certain embodiments, samples are stained such that a difference between the average optical density of the sample at one set of wavelengths and the average optical density of the sample at another set of wavelengths falls within a certain range or below a certain threshold. For example, a difference between the average optical density of the sample at green wavelengths and the average optical density of the sample at red wavelengths can be 0.08 or less (e.g., 0.07 or less, 0.06 or less, 0.05 or less, 0.04 or less, 0.03 or less, 0.01 or less). Red wavelengths can include wavelengths within a range from 610-650 nm, for example.

In some embodiments, sufficiently small quantities of eosin can be used to stain samples such that the contribution of eosin to the average optical density of the sample is less than a particular threshold value. For example, the contribution of eosin to the average optical density of the sample can be less than 0.08 (e.g., less than 0.06, less than 0.05, less than 0.04, less than 0.03, less than 0.02, less than 0.01).

To prepare eosin solutions suitable for use in the methods and systems disclosed herein, relatively small amounts of eosin can be used. For example, in some embodiments, the amount of eosin in a solution of 100 mL is 0.015 g or less (e.g., 0.01 g or less, 0.008 g or less, 0.006 g or less, 0.004 g or less, 0.002 g or less).

Spectral Imaging Systems

A variety of systems and techniques can be used to obtain spectral images and form spectral image cubes. For example, in some embodiments, spectral images can be obtained by using an imaging device (e.g., a camera such as a CCD camera) with one or more wavelength-selective filtering elements to allow a range of wavelengths of illumination light to reach the sample, and/or to allow a range of wavelengths of light from the sample to reach the imaging device. Varying the one or more wavelength-selective filtering elements to allow different ranges of wavelengths of illumination light and/or light from the sample to pass permits multiple two-dimensional images of the sample to be obtained, some or all of the two-dimensional images corresponding to different illumination and/or measurement wavelengths.

These two-dimensional images can be assembled to form a three-dimensional image cube. Two of the three dimensions in the image cube correspond to the two spatial dimensions common to each of the two-dimensional images. The third dimension of the image cube corresponds to a spectral dimension. That is, at each pixel location in the image cube, pixel values extending along the third dimension of the cube correspond to measurements of the same spatial location in the sample at different illumination wavelengths and/or different wavelengths of light from the sample. For each pixel in the two-dimensional spatial images of the sample, pixel values extending along the third dimension of the image cube correspond to information about wavelength-dependent properties of a particular spatial location in the sample. In some embodiments, for example, the wavelength-dependent information corresponds to a spectrum for some or all of the pixels. Thus, in general, image cubes include multiple individual image planes, some or all of which are acquired with different settings applied to the wavelength selective elements.

Image cubes can be analyzed in a variety of ways, including by using spectral unmixing methods. Typically, spectral unmixing techniques can be used together with a spectral library to analyze an image cube. A spectral library can include, for example, a set of wavelength-dependent functions, each of which can be associated with a different component in the sample.

Figure 18:
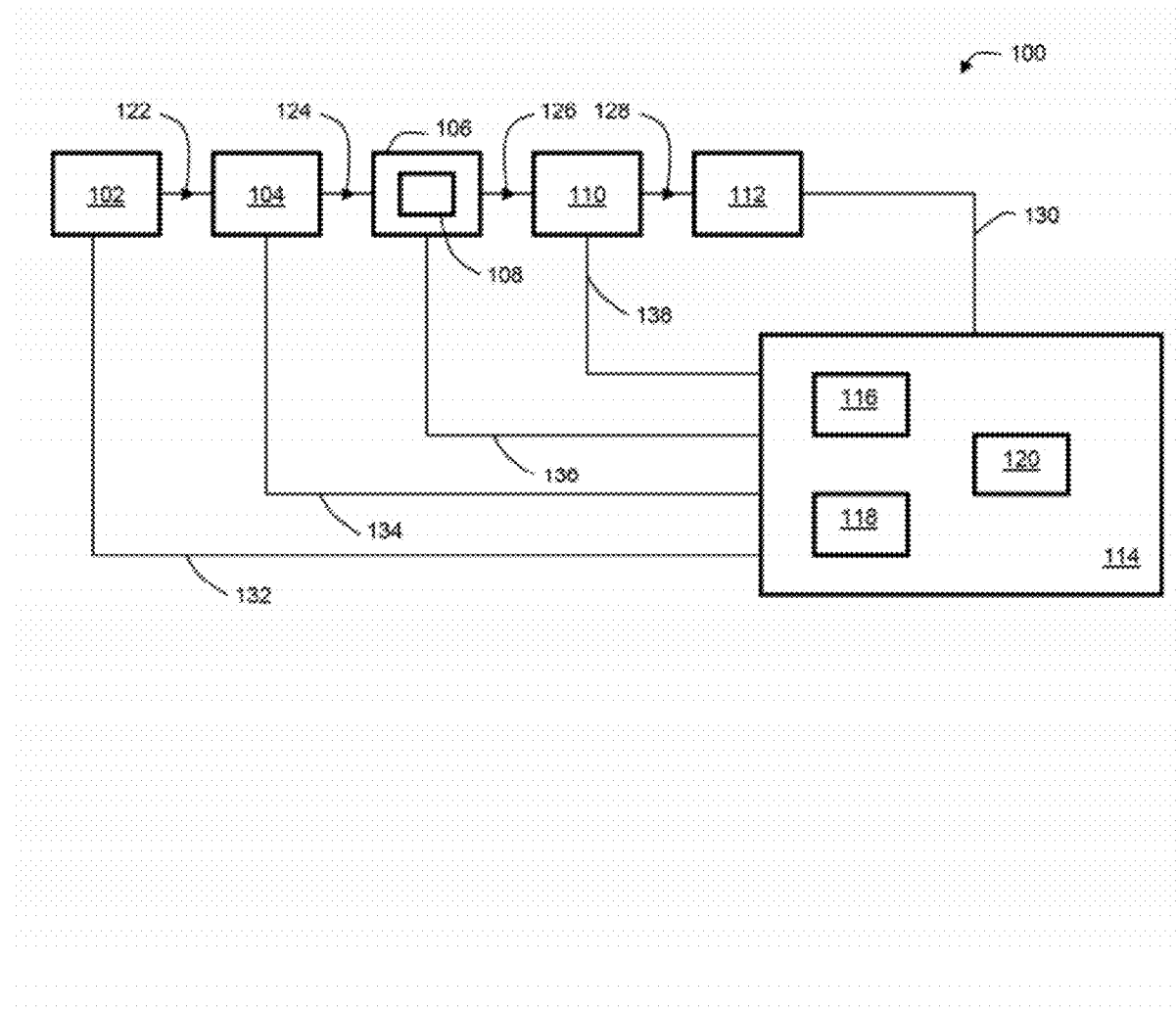
FIG. 18 shows a schematic diagram of a spectral imaging system.

FIG. 18 is a schematic diagram showing a system 100 for acquiring spectral images of a sample. A light source 102 provides light 122 to light conditioning optics 104. Light 122 can be incoherent light, such as light generated from a filament source for example, or light 122 can be coherent light, such as light generated by a laser. Light 122 can be either continuous-wave (CW) or time-gated (e.g., pulsed) light. Further, light 122 can be provided in a selected portion of the electromagnetic spectrum. For example, light 122 can have a central wavelength and/or a distribution of wavelengths that falls within the ultraviolet, visible, infrared, or other regions of the spectrum.

Light conditioning optics 104 can be configured to transform light 122 in a number of ways. For example, light conditioning optics 104 can spectrally filter light 122 to provide output light in a selected wavelength region of the spectrum. Alternatively, or in addition, light conditioning optics can adjust the spatial distribution of light 122 and the temporal properties of light 122. Incident light 124 is generated from light 122 by the action of the elements of light conditioning optics 104.

Incident light 124 is directed to be incident on sample 108 mounted on illumination stage 106. Stage 106 can provide means to secure sample 108, such as mounting clips or other fastening devices. Alternatively, stage 106 can include a movable track or belt on which a plurality of samples 108 are affixed. A driver mechanism can be configured to move the track in order to successively translate the plurality of samples, one at a time, through an illumination region on stage 106, whereon incident light 124 impinges. Stage 106 can further include translation axes and mechanisms for translating sample 108 relative to a fixed position of illumination stage 106. The translation mechanisms can be manually operated (e.g., threaded rods) or can be automatically movable via electrical actuation (e.g., motorized drivers, piezoelectric actuators).

In response to incident light 124, emitted light 126 emerges from sample 108. Emitted light 126 corresponds to fluorescence emission from sample 108 in response to incident light 124. In certain embodiments, sample 108 can be luminescent, and may produce emitted light 126 even in the temporary absence of incident light 124. In some embodiments, emitted light 126 can include light produced via two or more of the foregoing mechanisms.

Sample 108 can be a biological sample such as a tissue slice (e.g., a sample used for pathology), or a cell suspension or smear, as in cytology studies; or living or fixed cells in tissue culture. The present invention provides methods and apparatus for analyzing these types of samples.

Sample 108 can be rare-event cells such as circulating tumor cells, which may be present on a slide or may be contained in a sample chamber designed for the capture, concentration, or imaging of such cells. The present invention provides methods and apparatus for analyzing these types of samples.

Light collecting optics 110 are positioned to received emitted light 126 from sample 108. Light collecting optics 110 can be configured to collimate emitted light 126 when light 126 is divergent, for example. Light collecting optics 110 can also be configured to spectrally filter emitted light 126. Filtering operations can be useful, for example, to isolate portions of emitted light 126 arising via one of the mechanisms discussed above from light arising via other processes. Further, light collecting optics 110 can be configured to modify the spatial and/or temporal properties of emitted light 126 for particular purposes in embodiments. Light collecting optics 110 transform emitted light 126 into output light 128 which is incident on detector 112.

Detector 112 includes one or more elements such as CMOS or CCD sensors configured to detect output light 128. In some embodiments, detector 112 can be configured to measure the spatial and/or temporal and/or spectral properties of light 128. Detector 112 generates an electrical signal that corresponds to output light 128, and is communicated via electrical communication line 130 to electronic control system 114.

Electronic control system 114 includes a processor 116, a display device 118, and a user interface 120. In addition to receiving signals corresponding to output light 128 detected by detector 112, control system 114 sends electrical signals to detector 112 to adjust various properties of detector 112. For example, if detector 112 includes a CCD sensor, control system 114 can send electrical signals to detector 112 to control the exposure time, active area, gain settings, and other properties of the CCD sensor.

Electronic control system 114 can communicate with light source 102, light conditioning optics 104, illumination stage 106, and light collecting optics 110 via electrical communication lines 132, 134, 136, and 138, respectively. Control system 114 provides electrical signals to each of these elements of system 100 to adjust various properties of the elements. For example, electrical signals provided to light source 102 can adjust the intensity, wavelength, repetition rate, and/or other properties of light 122. Signals provided to light conditioning optics 104 and light collecting optics 110 can include signals for configuring properties of devices that adjust the spatial properties of light (e.g., spatial light modulators) and for configuring spectral filtering devices, for example. Signals provided to illumination stage 106 can provide for positioning of sample 108 relative to stage 106 and/or for moving samples into position for illumination on stage 106, for example.

Control system 114 includes a user interface 120 for displaying system properties and parameters, and for displaying captured images of sample 108. User interface 120 is provided in order to facilitate operator interaction with, and control over, system 100. Processor 116 is typically connected to a storage device for storing image data captured using detector 112, and also includes computer software that embodies instructions to processor 116 that cause processor 116 to carry out control functions, such as those discussed above for example. Further, the software instructions cause processor 116 to mathematically manipulate the images captured by detector 112 and to provide images of components in sample 108 derived from measured spectral images.

System 100 is often configured to acquire multiple spectral images of sample 108. The multiple spectral images may correspond to illumination of sample 108 at one or more wavelengths of light, and detecting an intensity of light produced by sample 108. Alternatively, the multiple spectral images may correspond to illumination of sample 108 with light having similar spectral properties, and collecting multiple images of sample 108, each image corresponding to a different wavelength of emitted light 126. Spectral filtering elements in light conditioning optics 104 and light collecting optics 110 are generally used to obtain the spectrally resolved data. In some embodiments, the multiple spectral images can include both images corresponding to illumination of sample 108 with different wavelengths of light, and images corresponding to different wavelengths of emitted light from sample 108.

In some embodiments, images of sample 108 can be collected in sequence, with adjustments to the configuration of optical components (e.g., optical filters) between successive captured images. In certain embodiments, multiple images can be captured simultaneously using detection systems configured to detect multiple sample views. For example, detection systems can be configured to project different views of the sample corresponding to different illumination or emission wavelengths onto a detector such as a CMOS sensor or CCD camera, and the multiple views can be captured simultaneously.

In some embodiments, light conditioning optics 104 include an adjustable spectral filter element such as a filter wheel or a liquid crystal spectral filter. The filter element can be configured to provide for illumination of sample 108 using different light wavelength bands. Light source 102 can provide light 122 having a broad distribution of spectral wavelength components. A selected region of this broad wavelength distribution is allowed to pass as incident light 124 by the filter element in light conditioning optics 104, and directed to be incident on sample 108.

In general, as used herein, an image is a measurement of an intensity distribution of light emitted by the sample as a function of position within the sample. Typically, measured images are two-dimensional so that the intensity distribution is expressed as a function of two position coordinates.

Exemplary spectral filtering elements that can be used in both light conditioning optics 104 and light collecting optics 110 include, for example, liquid-crystal tunable filters (LCTFs) and acousto-optic tunable filters (AOTFs). Other exemplary spectral filtering elements include mechanical filter wheels with multiple optical filters that can be engaged in sequence (e.g., by rotating the wheel). Exemplary wavelength-selective elements can also include one or more configurable light sources 102 that generate light 122. Light sources 102 can be adjusted to produce light 122 in one or more selected wavelength bands, for example. Light sources can be constructed using multiple light emitting diodes (LEDs), some or all of which emit light in different regions of the electromagnetic spectrum. Alternatively, or in addition, light sources 102 can include broadband light sources in combination with wavelength selecting elements such as diffraction gratings and spatial light modulators (e.g., a digital micromirror device (DMD), available from Texas Instruments, Dallas, Tex.). The wavelength selecting elements can be configured so that only certain wavelengths of light generated by the broadband sources are incident on sample 108.

In some embodiments, wavelength-selective filtering can be performed by a Sagnac interferometer, a liquid crystal interferometer, or another type of imaging interferometer-based detection system. At a selected time, an interferometer measures a spectral response for a sample that is a periodic function of wavelength rather than a single well-defined wavelength band. The response of an interferometer is characterized by an optical path difference $\Delta$ which defines the periodic wavelength function. Interferometric images can be unmixed directly to yield component estimates in frequency space. Alternatively, images obtained using an interferometer can be transformed into a set of spectral images at particular wavelengths (e.g., central wavelengths) by applying a Fourier transform or a similar operation to the images. Spectral images obtained by transforming images from an interferometer can form planes of an image cube corresponding to specific wavelength bands, and can be used as input data for overlapping unmixing. Further, spectral images derived from interferometer images can be used as input data for incremental unmixing operations.

Because both light conditioning optics 104 and light collecting optics 110 can include configurable spectral filter elements, spectral resolution can be provided either on the excitation side of sample 108 (e.g., via light conditioning optics 104) or on the emission side of sample 108 (e.g., via light collecting optics 110), or both. The multiple, spectrally resolved images of sample 108 form an image cube as discussed above, where each image in the cube is a two-dimensional image of the sample corresponding to a particular wavelength. The third cube dimension corresponds to spectral wavelength, and wavelength-dependent information about particular spatial locations within the sample (e.g., as represented by pixels in the spectral images) extends along the third dimension. As used herein, a pixel corresponds nominally to a common spatial location in the sample for each of the spectral images in an image cube.

Spectral Unmixing

Spectral unmixing is a mathematical operation performed on an image cube to provide quantitative estimates of the amounts of each of several components present in a sample. In some embodiments, spectral unmixing techniques reference one or more spectral libraries that include information about spectral properties of sample components. Typically, spectral unmixing techniques are applied to each pixel along each of the two spatial dimensions of an image cube. The result of the unmixing operations is a high resolution map of each of the components (e.g., chemical entities and/or conditions) that are present in the sample.

As an example, a sample may contain three different types of structures, each labeled with a different dye. The three different dyes may each have different absorption spectra. Typically, the individual absorption spectra of the dyes are known before they are used (e.g., from a spectral library), or they can be measured. Images of the illuminated sample will contain, in the most general case, spectral contributions from each of the three dyes. A similar situation arises, for example, in samples containing multiple different fluorescence labels, each of which contribute to measured fluorescence emission from the sample.

Spectral unmixing decomposes one or more images that include contributions from multiple spectral sources into a set of component images (the "unmixed images") that correspond to contributions from each of the spectral entities within the sample. Thus, if the sample includes three different dyes, each specific to a particular structural entity, then an image of the sample can be separated into three unmixed images, each unmixed image reflecting contributions principally from only one of the dyes. In general, as used herein, the term "component" refers to an entity (a chemical moiety, a biological entity, or any other entity) that contributes to radiation that is detected from a sample. Thus, a sample's components each contribute to the radiation emanating from the sample. Each of the components has a spectral signature or eigenstate that describes its pure spectral properties (e.g., the spectral properties of the component with no other components present). Further, the term "component image," as used herein, refers to an image of a sample that includes (substantially) only contributions from a single component of the sample; that is, an image of the sample with spectral properties that can be expressed in terms of a single component's spectral signature or eigenstate. The process of "unmixing," as used herein, refers to a process in which a sample image that includes contributions from multiple components is separated into a set of unmixed images, each unmixed image including contributions from only a subset of the components in the sample. If the unmixed images each include contributions from only one component in the sample, the unmixed images are component images.

The unmixing procedure essentially corresponds to decomposing an image into a set of spectral eigenstates. In some embodiments, the eigenstates are known beforehand, as discussed above. In certain embodiments, the eigenstates can sometimes be determined using techniques such as principal component analysis. In either case, once the eigenstates have been identified or estimated, an image can be decomposed by calculating a set of values, usually as a coefficient matrix, that corresponds to the relative weighting of each of the eigenstates in the overall image. The contributions of each of the individual eigenstates can then be separated out to yield the unmixed image set.

As an example, a series of two dimensional images having x and y coordinates can be measured for a sample by illuminating the sample at a set of different excitation wavelengths $\lambda_k$. As described above, the two dimensional images can be combined to form a three-dimensional image cube $S(x,y,k)$ where the first two indices of the image cube represent coordinate directions, and the third index is a spectral index corresponding to the wavelength of the illumination light. Assuming, for the sake of simplicity, that each of the images of the sample contains spectral contributions from two different spectral sources $F(\lambda_k)$ and $G(\lambda_k)$, then the values in the three-dimensional image cube $S(x,y,k)$ may be given by $$S(x,y,k)=a(x,y) \cdot F(\lambda_k)+b(x,y) \cdot G(\lambda_k) \qquad (1)$$

where $\lambda_k$ is used to denote a given wavelength (or wavelength band). The functions $a(x,y)$ and $b(x,y)$ describe the spatial abundance of the spectral contributions from the two different spectral sources in the sample.

According to Equation (1), the net signal at any position in the three-dimensional image cube (e.g., at any two-dimensional pixel coordinate, and at a particular illumination wavelength) is the sum of two contributions, weighted by the relative abundance of each. This can be expressed as $$S(\lambda_k)=aF(\lambda_k)+bG(\lambda_k) \qquad (2)$$

The functions F and G can be termed the "spectral eigenstates" for the system because they correspond to the pure spectra for the spectral sources in the sample, which are combined in varying proportions to produce the measured spectral images of the sample. Thus, the sample spectrum is a weighted superposition corresponding to separate contributions from the two spectral sources.

If the spectra $F(\lambda_k)$ and $G(\lambda_k)$ are known (or can be deduced), then Equation (2) can be inverted to solve for a and b, provided that spectrum I includes at least two elements (e.g., provided that one has data for at least two wavelengths $\lambda_k$). Equation (2) can be rewritten in matrix form as S=EA, so that $$A=E^{-1}S \qquad (3)$$

where A is a column vector with components a and b, and E is a matrix whose columns are the spectral eigenstates, namely [F G].

Using Equation (3), measured spectral images of a sample can be used to calculate contributions to the images arising purely from source F and purely from source G at particular pixel locations. The process can be repeated for each pixel location in a selected image (e.g., throughout the range of values x and y in S) to produce an image of the sample that includes contributions only from source F, and another image of the sample that includes contributions only from source G.

In the above discussion, the number of spectral sources is two (e.g., F and G). In general, however, unmixing techniques are not restricted to any particular number of sources. For example, a sample can generally contain N different spectral sources. If the number of wavelengths at which data is collected is M—that is, k=1 . . . M—then matrix E is an M×N matrix instead of an M×2 matrix, as in the above discussion. The unmixing algorithm can then be employed in the same manner as described above to isolate specific contributions at each pixel location in an image from each of the N spectral eigenstates.

One factor which can limit the ability of the algorithm to distinguish between contributions from different spectral eigenstates is the degree of spectral distinction between the eigenstates. The correlation between two spectra, such as two spectral eigenstates $I_1$ and $I_2$, can be described by a spectral angle $\theta$ where $$\theta = \cos^{-1}\left[\frac{I_1 \cdot I_2}{|I_1||I_2|}\right] \quad (4)$$

Sets of spectra for which $\theta$ is small for two members are not as easily separated into their components. Physically, the reason for this is easily understood: if two spectra are only marginally different, it is harder to determine the relative abundance of each.

A number of techniques can be used to measure or estimate the pure spectra of the spectral sources F and G (and other spectral sources, where the sample includes more than two). In general, any method that yields spectral eigenstates of sufficient accuracy can be used. Some samples can contain spectral sources such as dyes, fluorescence labels, or other chemical moieties for which there are known spectra available in published reference materials. Alternatively, it may be possible to directly measure the spectra of source components using one or more measurement systems. In some samples, a particular region of the sample may be known to include only one particular spectral source, and the spectrum of that source can be extracted from measurements taken on only the identified region of the sample.

Various data analysis techniques can also be used for determining component spectra for spectral unmixing, such as principal component analysis (PCA), which identifies the most orthogonal spectral eigenvectors from an image cube and yields score images showing the weighting of each eigenvector throughout the image. This may be done in combination with other mathematical processing, and there are other known techniques for identifying low-dimensionality spectral vectors, such as projection pursuit, a technique described, for example, in L. Jimenez and D. Landgrebe, "Hyperspectral Data Analysis and Feature Reduction Via Projection Pursuit", *IEEE Transactions on Geoscience and Remote Sensing*, Vol. 37, No. 6, pp. 2653-2667, November 1999, the entire contents of which are incorporated herein by reference. Other techniques include independent component analysis (ICA) and end-member detection algorithms, for example.

These techniques are typically not well-suited to the applications in the life sciences. For example, some techniques are optimized for spectral imaging data sets that contain spectra with dense spectral shapes and well-defined narrow peaks. In some techniques the spectral ranges are large compared to the individual spectral features and peaks that are used for analysis. The presence of peaks, or the ratio of peaks, may be then used to classify "end-members" to be separated. Typically, the components in biological samples do not have well-defined, narrow peaks.

Some of these techniques generate images related to spectra that are present in a pure form somewhere within the original image cube. In many cases in the life sciences, signal spectra present in the image cube are mixtures of components. If the component of interest is not in a pure form somewhere in the original image cube, then it is unlikely that these techniques will generate an image that accurately represents the abundance of the component of interest. There are some techniques, sometimes called "convex-hull" algorithms, that estimate what the true end-members are even if they do not exist in a pure form in the image, but the effectiveness is dependent on how close signal spectra in the image cube are to the end-members.

One technique that can be used to extract spectral eigenstates (or representations thereof) without a priori knowledge of all of the eigenstates involves considering the signal spectrum $S(\lambda_k)$ for a given pixel, and subtracting from it the maximum amount of a first spectral source $F(\lambda_k)$ while leaving the remaining signal that is positive definite in all spectral channels. That is, one defines a so-called "remainder spectrum" $U_a(\lambda_k)$ for each pixel as $$U_a(\lambda_k) = S(\lambda_k) - aF(\lambda_k) \quad (5)$$

and then selects the largest value of the parameter a consistent with $U_a(\lambda_k)$ having a non-negative value in every spectral channel. The resulting spectrum $U_a(\lambda_k)$ is then used as the signal spectrum, expunged of contributions due to first spectral source F. One may also make the determination of parameter a based not on the strict non-negative criterion listed above, but on some related criterion that incorporates a small negative distribution to account for considerations such as shot noise or detector noise in a measurement system. Additional examples of optimization criteria for removing the maximal amount of spectral source F include using different error functions.

Alternatively, one may seek to extract a contribution to a measured spectrum that is due to second spectral source G. In analogy with Equation (5), the remainder spectrum can be calculated for each pixel as $$U_b(\lambda_k) = S(\lambda_k) - bG(\lambda_k) \quad (6)$$

where one selects the largest value of the parameter b consistent with $U_b(\lambda_k)$ having a non-negative value in every spectral channel.

The remainder technique can be expanded to cases where the spectra for one or more additional components of the sample are known, and one wants to remove their contributions to the signal. In such cases, the remainder spectrum is written to subtract a contribution of each such component from the observed signal based on the additional spectra and consistent with a positive remainder in each spectral channel.

Additional spectral unmixing techniques are described in PCT Patent Application Publication No. WO2005/040769 entitled "SPECTRAL IMAGING OF BIOLOGICAL SAMPLES," the entire contents of which are incorporated herein by reference.

In order for the spectral unmixing techniques disclosed herein to effectively separate contributions in sample images that are due to different spectral eigenstates, Equation (1) should be at least approximately correct. That is, the measured spectral data should be approximately described as a linear superposition of weighted eigenstates. This approximation holds for many samples and spectral measurement techniques, especially darkfield measurement techniques.

Hardware and Software

The steps described above in connection with various methods for collecting, processing, analyzing, interpreting, and displaying information from samples can be implemented in computer programs using standard programming techniques, including steps associated with spectral unmixing and creating synthetic absorption images of samples. Such programs are designed to execute on programmable computers or specifically designed integrated circuits, each comprising an electronic processor, a data storage system (including memory and/or storage elements), at least one input device, and least one output device, such as a display or printer. The program code is applied to input data (e.g., images from the detector) to perform the functions described herein and generate output information (e.g., images showing contributions of sample components, overlays of multiple component images, etc.), which is applied to one or more output devices, such as a user interface that includes a display device. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis and control functions described herein.

EXAMPLES

The disclosure includes the following examples, which are not intended to limit the scope of the claims. In this disclosure, the term eosin is used to mean any of eosin Y, eosin B, phloxine B, and compounds that stain biological structures similarly to any of these (such structures being known as eosinophilic), as well as mixtures of any of such compounds. Eosin Y is a tetrabromo derivate of fluorescein and eosin B is a dibromo dinitro derivative of fluorescein. In its deprotonated form, eosin Y can be described as 2-(2,4,5,7-tetrabromo-6-oxido-3-oxo-3H-xanthen-9-yl) benzoate (CAS number 17372-87-1). Eosin Y can be described as 4',5'-dibromo-3',6'-dihydroxy-2',7'-dinitro-1-spiro[isobenzofuran-3,9'-xanthene]one (CAS 548-24-3). Phloxine B can be described as disodium 2',4',5',7'-tetrabromo-4,5,6,7-tetrachloro-3-oxospiro[2-benzofuran-1,9'-xanthene]-3',6'-diolate (CAS number 18472-87-2). In the examples below, these more specific terms are used in some cases, to denote the specific compounds used.

In a first experiment, human breast cancer tissue samples (obtained from U.S. Biomax, Rockville Md.) were prepared with an immunofluorescence assay, using a mouse anti-Her2 antibody raised from a human sequence (obtained from Abcam, Inc., Cambridge, Mass.) at 1:25 dilution and a fluorochrome stain (ALEXA FLUOR® 594 dye) conjugated to a goat anti-mouse secondary antibody (obtained from Invitrogen, Carlsbad, Calif.) at 1:50 dilution. The samples were then stained with a DAPI nuclear stain at 1:20,000 dilution and imaged using a Nuance FX multispectral imaging camera (available from Caliper Life Sciences, Hopkinton, Mass.) on an Olympus BX51 microscope. A brightfield image of the sample was obtained and converted to optical density units using Nuance 2.10 software (available from Caliper Life Sciences), and the green channel was exported. FIG. 2A shows a green channel image for one of the samples. The image shows a faint amount of absorption, and while one could discern where the tissue was present, the overall image shows little contrast and the tissue structures were difficult to identify.

Next, a working solution of eosin was prepared using 100 mL of 1% eosin Y, 10 mL of 1% phloxine B, 780 mL of ethanol, and 4 mL of glacial acetic acid. This protocol is endorsed by its authors for use in preparing samples for bright-field imaging, where the recommended procedure is to apply the working solution to the tissue for 30 seconds to 1 minute. A complete description of the protocol is available at internet address protocolsonline.com, under the histology section covering hematoxylin and eosin staining.

The working solution was then subjected to 1:100 dilution using a mixture of 780 parts ethanol and 4 parts glacial acetic acid, for a net concentration of 0.0011% eosin Y and 0.00011% phloxine B. The sample was placed in this mixture for 20 seconds, then rinsed with a buffer solution and imaged using the Nuance camera and the Olympus microscope.

A brightfield image of the sample was again obtained and the optical density image was generated and exported. The green channel of this image is shown in FIG. 2B. Visually, there was little change from the appearance prior to staining, with little or no contrast or visual appearance of color when the sample was viewed in brightfield mode.

Figure 3B:
Figure 3C:

Fluorescent imaging was then performed using the same microscope and camera, together with a 200 Watt metal-halide arc light source (obtained from Prior Scientific, Rockland, Md.). A Chroma 11000V3 interference filter set (obtained from Chroma Technology Corp., Bellows Falls, Vt.) was used to image fluorescence emission in the range 440-660 nm, and a Chroma 49004 ET interference filter set (also obtained from Chroma Technology Corp.) was used to image fluorescence emission in the range 560-680, using 20 nm increments throughout. The fluorescence image cubes obtained in this manner were rendered as a color image by the Nuance software, and the individual blue, green, and red channels are shown in FIGS. 3A, 3B, and 3C.

Figure 3D:
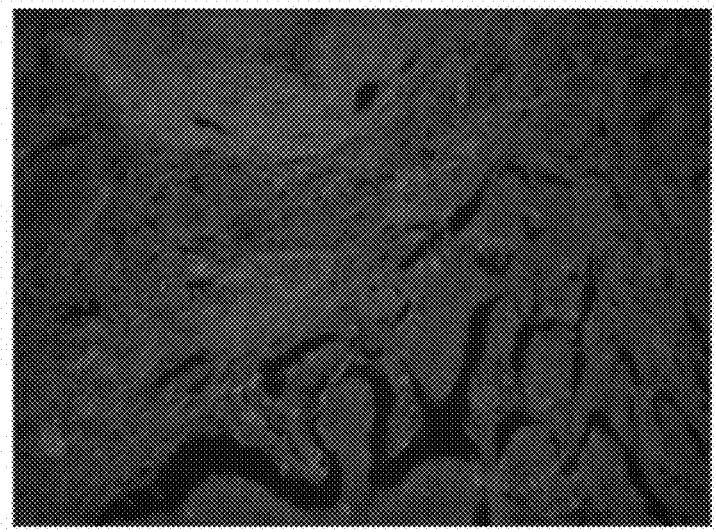
FIGS. 3D, 3E, and 3F are fluorescence emission images of the sample of FIG. 2C in blue, green, and red regions of the electromagnetic spectrum, respectively.
Figure 3E:
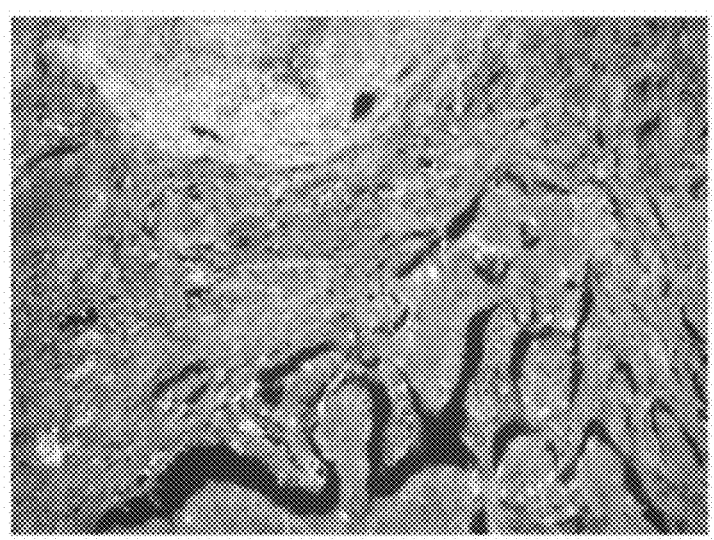
Figure 3F:

The sample was then subjected to 20 seconds in the working eosin solution, and imaged again using an identical imaging protocol. At this point, the sample was clearly visible and had a pink color. The green channel of the brightfield image is shown as FIG. 2C. Fluorescence imaging was then performed using the same filter sets and wavelength ranges as before, obtaining a fluorescence image cube for the sample. The individual blue, green, and red channels of the cube are shown in FIGS. 3D, 3E, and 3F.

Spectral libraries were developed to unmix the fluorescence image cubes into component images, based on additional samples of breast cancer tissue. A first tissue sample was stained only with DAPI, a second was prepared with the Her2 label. These samples were imaged, and representative regions that expressed these components were selected using the Nuance spectral library software. Another sample which had not had any stain applied was measured to provide an estimate of the tissue autofluorescence spectrum. The eosin mixture was measured directly from the sample, after being subjected to the working solution bath.

Figure 4A:
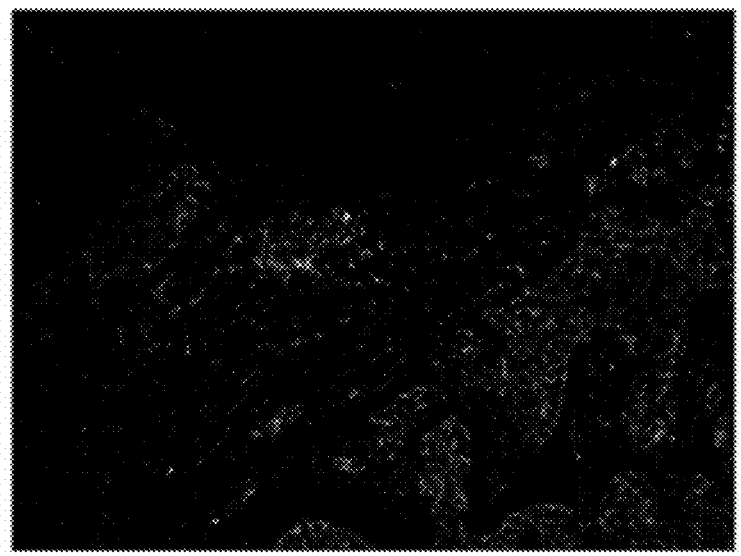
FIGS. 4A and 4B are component images of the sample of FIG. 2B corresponding to the Her2 and DAPI component signals, respectively, obtained by unmixing a multispectral fluorescence image of the sample.
Figure 4B:
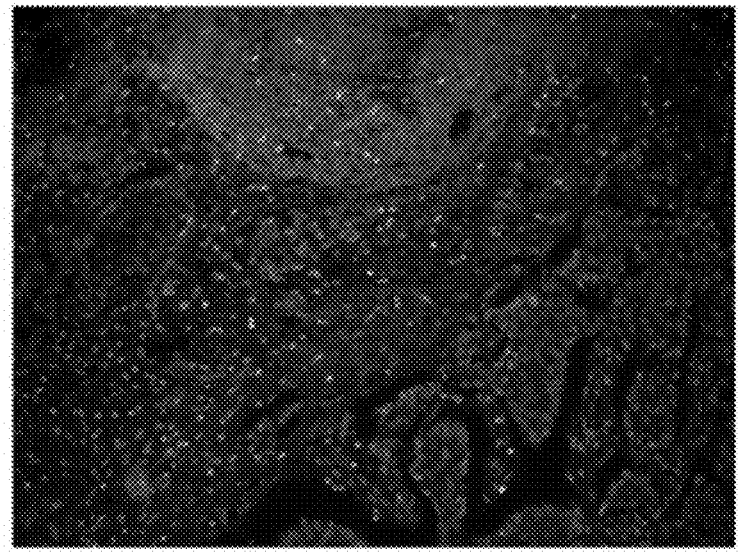
Figure 5A:
FIGS. 5A and 5B are component images of the sample of FIG. 2C corresponding to the Her2 and DAPI component signals, respectively, obtained by unmixing a multispectral fluorescence image of the sample.
Figure 5B:
Figure 6A:
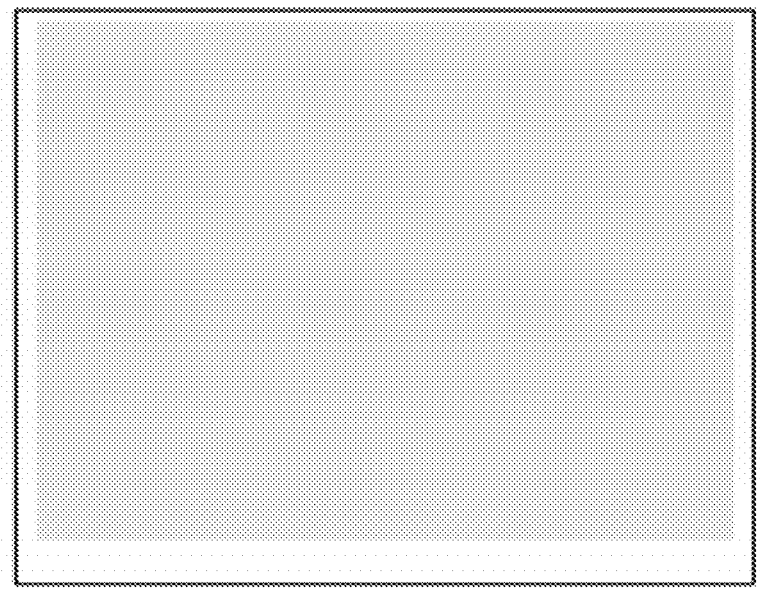
FIGS. 6A, 6B, and 6C are images that correspond to the blue, green, and red channels, respectively, of a synthetic transmitted-light H&E image of the sample of FIG. 2B, where a full multi-spectral image cube was acquired and then spectrally unmixed to produce estimates of the DAPI, eosin, fluorochrome stain (ALEXA FLUOR® 594), and tissue autofluorescence contributions at each pixel, and the synthetic transmitted-light H&E image was produced by rendering the DAPI signal in blue and the eosin signal in pink on a white background.
Figure 6B:
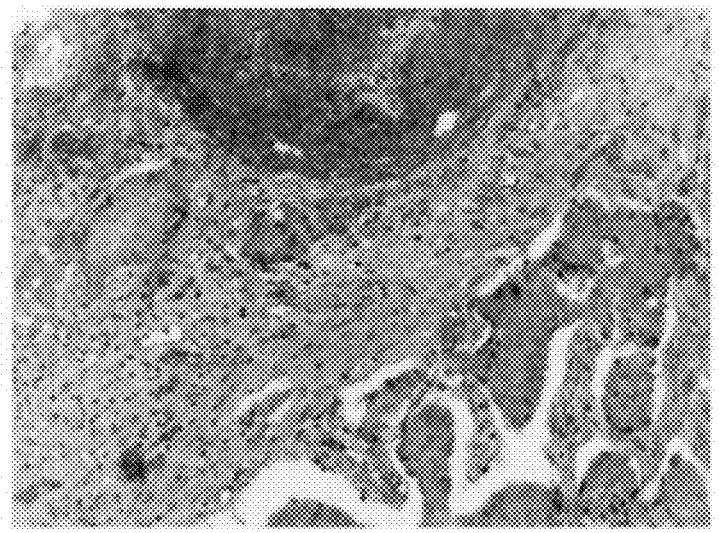
Figure 6C:
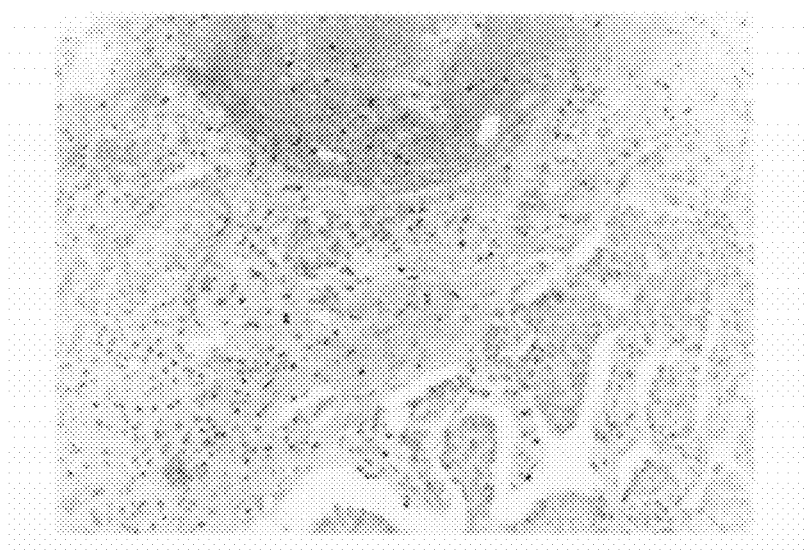

The image cubes of the sample after exposure to the 1:100 dilution eosin, and after exposure to working strength eosin, were unmixed using the Nuance software using the spectral libraries described above. The component images corresponding to the DAPI and Her2 components are shown in FIGS. 4A and 4B after the 1:100 staining, and in FIGS. 5A and 5B after the working strength staining. In FIGS. 4A and 4B, the DAPI component image shows good localization in the nuclei, and the Her2 is present in membrane structures within the cancerous region of the sample, as expected. However, in FIGS. 5A and 5B, the DAPI image shows no nuclei and the Her2 imagery, though approximately localized to the cancerous regions, is of low quality.

Figure 7A:
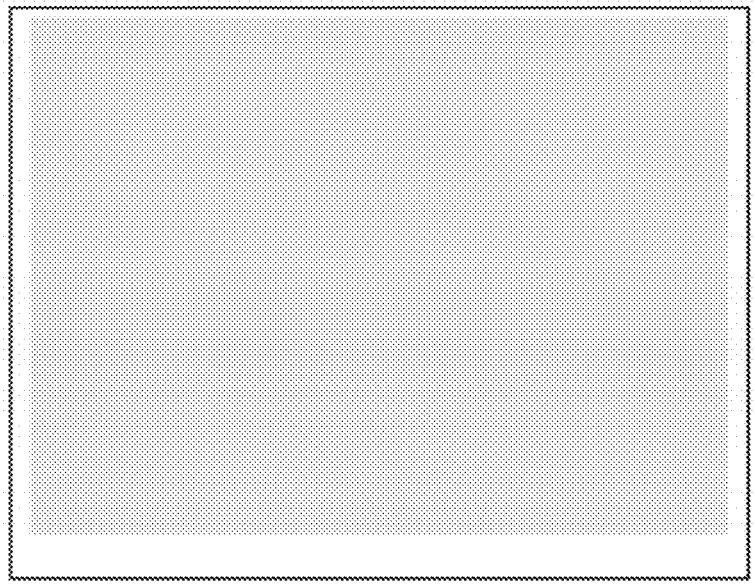
FIGS. 7A, 7B, and 7C are images that correspond to the blue, green, and red channels, respectively, of a synthetic transmitted-light H&E image of the sample of FIG. 2C, where a full multi-spectral image cube was acquired and then spectrally unmixed to produce estimates of the DAPI, eosin, fluorochrome stain (ALEXA FLUOR® 594), and tissue autofluorescence contributions at each pixel, and the synthetic transmitted-light H&E image was produced by rendering the DAPI signal in blue and the eosin signal in pink on white background.
Figure 7B:
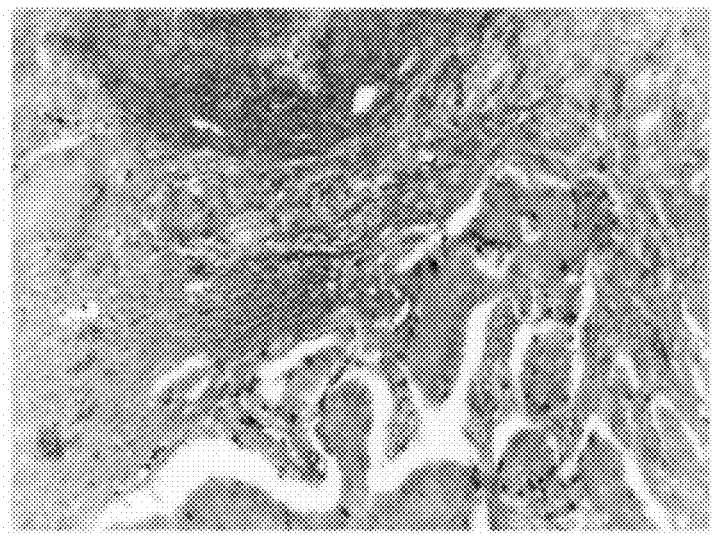
Figure 7C:
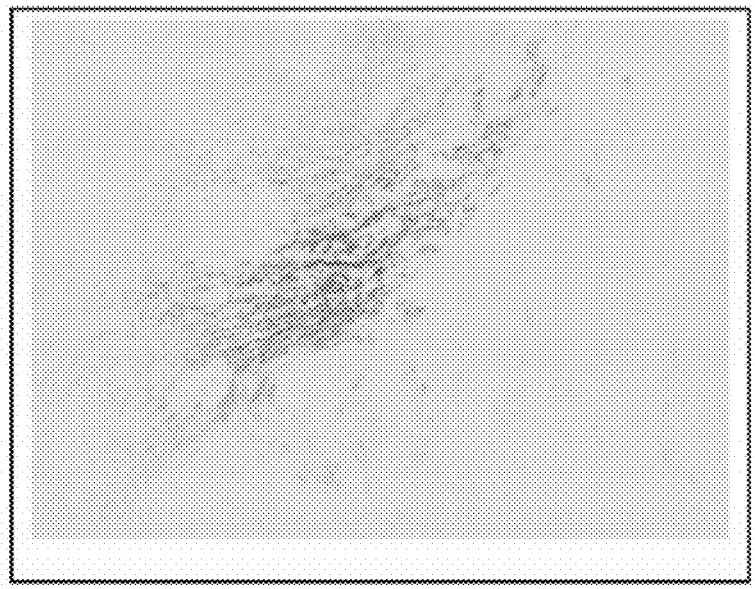
Figure 19:
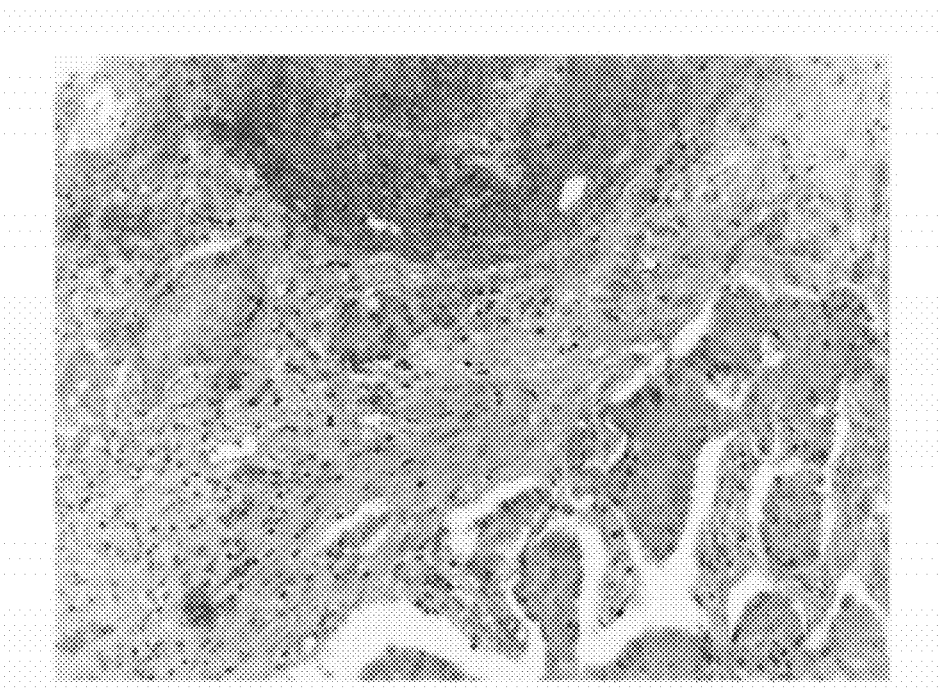
FIG. 19 shows an image that corresponds to the combined images of FIGS. 6A-6C.
Figure 20:
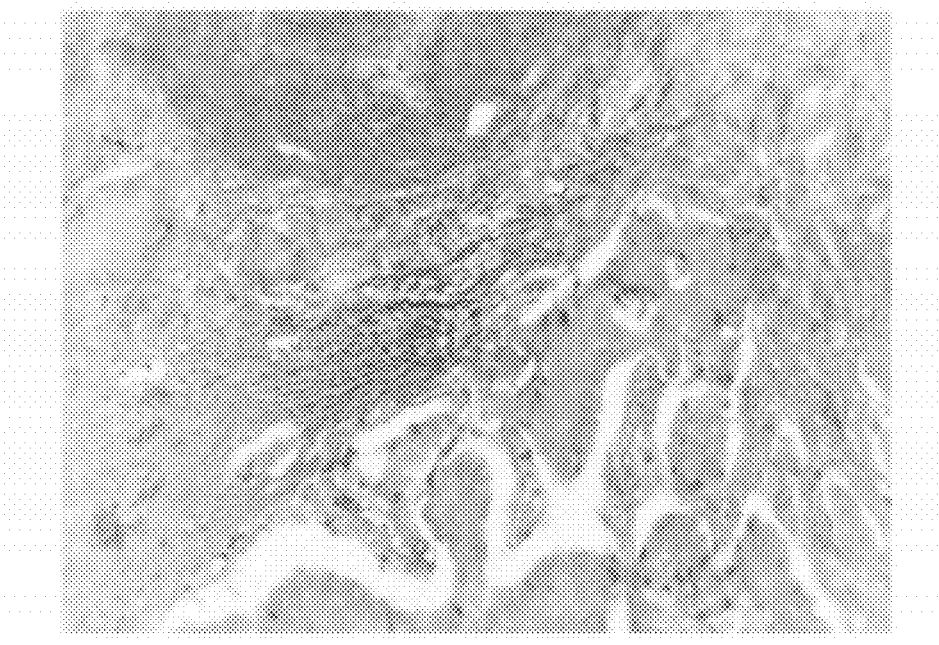
FIG. 20 shows an image that corresponds to the combined images of FIGS. 7A-7C.

A synthetic brightfield image was generated using the composite tool in the Nuance software, where the DAPI channel was mapped to a blue color and the eosin channel was mapped to a pink color. The resulting images shown in FIGS. 6A, 6B, and 6C for the 1:100 dilution eosin staining protocol, and in FIGS. 7A, 7B, and 7C for the working strength eosin staining protocol. In addition, FIG. 19 shows an image that corresponds to a combination of the images of FIGS. 6A-6C, and FIG. 20 shows an image that corresponds to a combination of the images of FIGS. 7A-7C. The imagery for the 1:100 dilution protocol showed a good resemblance to the brightfield view of a standard H&E preparation, whereas the working solution protocol failed to show the tissue landmarks in recognizable form.

Figure 8A:
FIGS. 8A, 8B, and 8C are images that correspond to blue, green, and red fluorescence emission, respectively, from a sample prepared with DAPI and quantum dots that emit at 605 nm conjugated to Her2, followed by a dilute eosin staining protocol of 0.0011% eosin Y and 0.00011% phlozine B for 20 seconds.
Figure 8B:
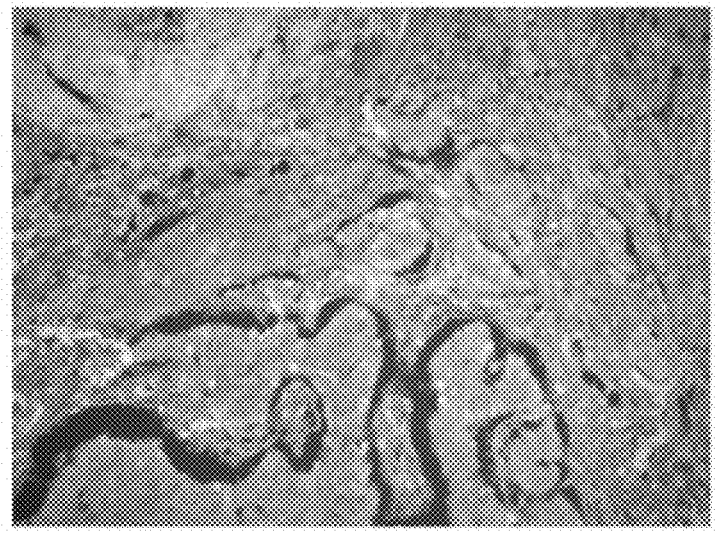
Figure 8C:

A second experiment was performed using serial sections from the same tissue block, and the same primary antibody, as described above. However, the Her2 probe used quantum dots that emit at 605 nm, conjugated to goat anti-mouse secondary antibodies (obtained from Invitrogen). These were used at 25:1 dilution. DAPI was applied in a 1:50,000 concentration and eosin was applied in a 1:100 concentration from working solutions described above, for a 20 second exposure time in the bath. Fluorescent imaging was then performed using the same equipment described above, but images were obtained at wavelengths only in the 440-660 nm range using the Chroma 11000V3 interference filter set. The blue, green, and red component images of the fluorescent image cube obtained using the Nuance software are shown in FIGS. 8A, 8B and 8C. For ease of comparison, approximately the same spatial region of tissue was imaged as in the first experiment above.

Figure 9:
FIG. 9 is an image of the Her2 component fluorescence signal obtained by unmixing a multispectral fluorescent image of the sample of FIGS. 8A-8C.

A spectral estimate of the quantum dot probe was obtained by imaging a different sample which had been prepared with only this stain, and had not been subjected to DAPI or eosin staining. The Nuance software was used to spectrally unmix the image cube, using the spectral library estimates for DAPI, tissue, eosin, and the quantum dot probe. The Her2 component image is shown in FIG. 9, and exhibits good localization of signal in membranes within the cancerous regions of the sample.

Figure 10A:
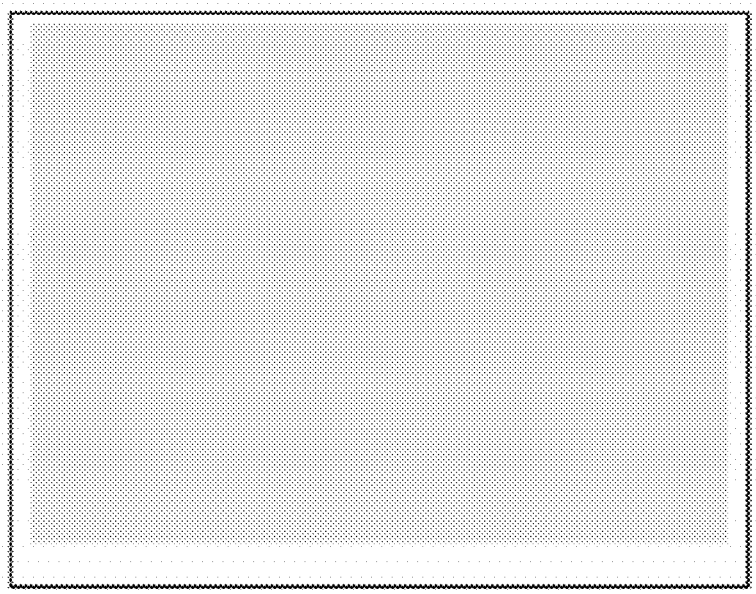
FIGS. 10A, 10B, and 10C are images that correspond to the blue, green, and red channels, respectively, of a synthetic transmitted-light H&E image of the sample of FIGS. 8A-8C, where a full multi-spectral image cube was acquired and then spectrally unmixed to produce estimates of the DAPI, eosin, and quantum dot contributions at each pixel, and the synthetic transmitted-light H&E image was produced by rendering the DAPI signal in blue and rendering the eosin signal in pink on a white background.
Figure 10B:
Figure 10C:
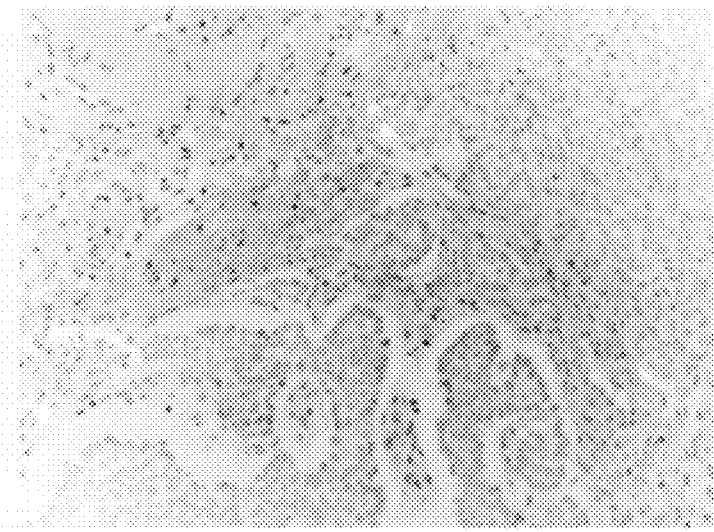
Figure 21:
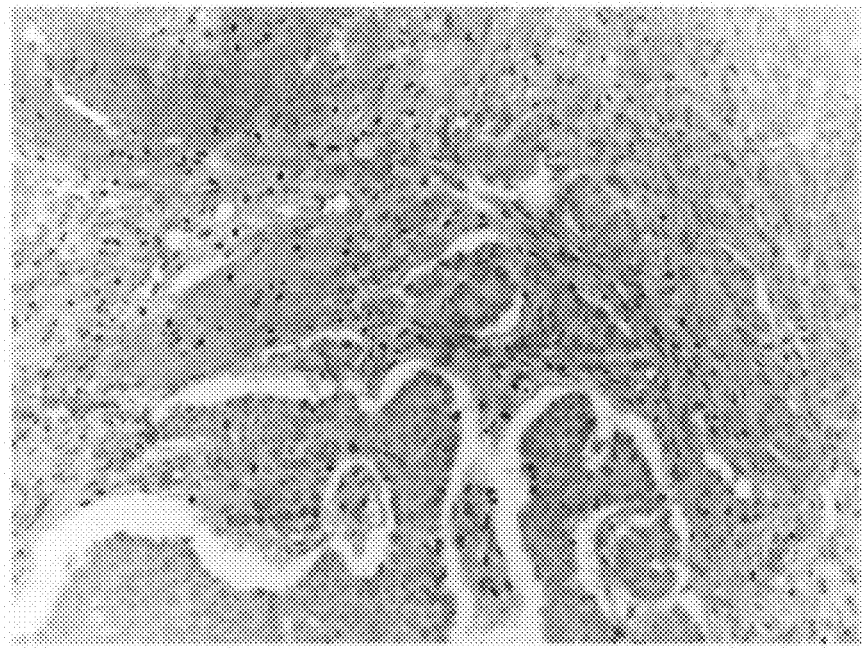
FIG. 21 shows an image that corresponds to the combined images of FIGS. 10A-10C.

As before, a synthetic brightfield view was created that mapped the DAPI component to a blue color and the eosin component to a pink color. This produced a view that was very similar to H&E preparations of similar samples when viewed in a brightfield microscope. The individual color planes of the synthetic image are shown in FIGS. 10A, 10B, and 10C. In addition, FIG. 21 shows an image that corresponds to a combination of the images of FIGS. 10A-10C.

A third experiment was performed using tissue from the same block. In the third experiment, the DAPI and the Her2 probe were identical to those used in the first experiment described above. However, a different eosin preparation was used. In this experiment, 1 gram of phloxine B was dissolved in 100 mL of water to make a working eosin solution. This working solution was then diluted in a 50:1 ratio with water, and the sample was placed in this bath for 20 seconds.

Figure 12A:
FIG. 12A is a transmitted-light image of a sample prepared with DAPI and an IF label based on a fluorochrome stain (ALEXA FLUOR® 594), and further prepared with a dilute eosin protocol of 0.02% phloxine B for 20 seconds.
Figure 13A:
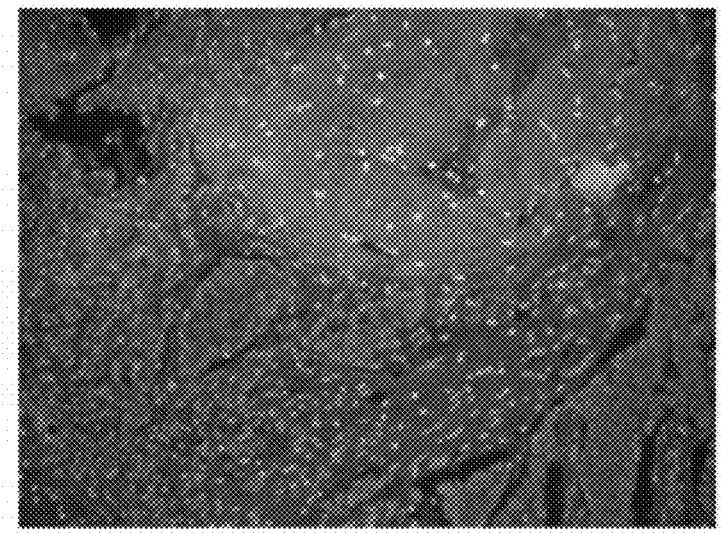
FIGS. 13A, 13B, and 13C are images that correspond to blue, green, and red fluorescence emission, respectively, from the sample of FIG. 12A.
Figure 13B:
Figure 13C:
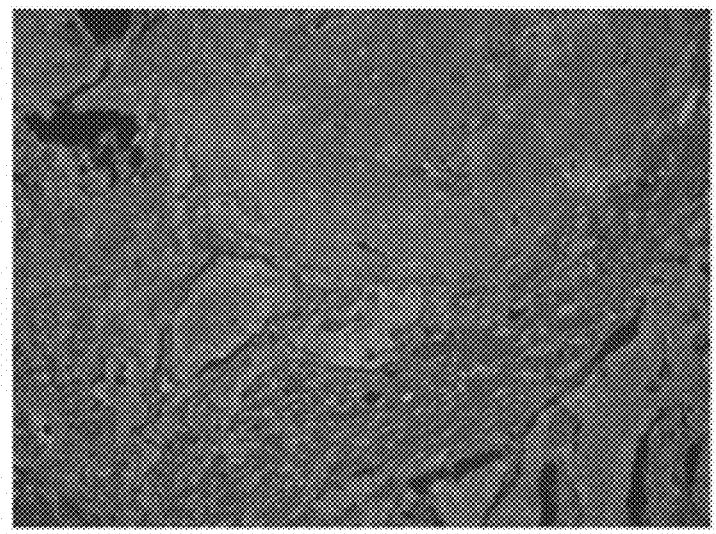

The sample was then placed in the microscope and imaged in brightfield using the camera to obtain optical density images of its absorption. The green channel of one such image is shown in FIG. 12A. As before, there was little contrast or color observable when the sample was viewed in the brightfield microscope. Fluorescence images were taken using the wavelength ranges and filter sets described above in the first experiment, to obtain a fluorescence spectral cube. The blue, green, and red component images from the cube are shown as FIGS. 13A, 13B, and 13C.

Figure 12B:
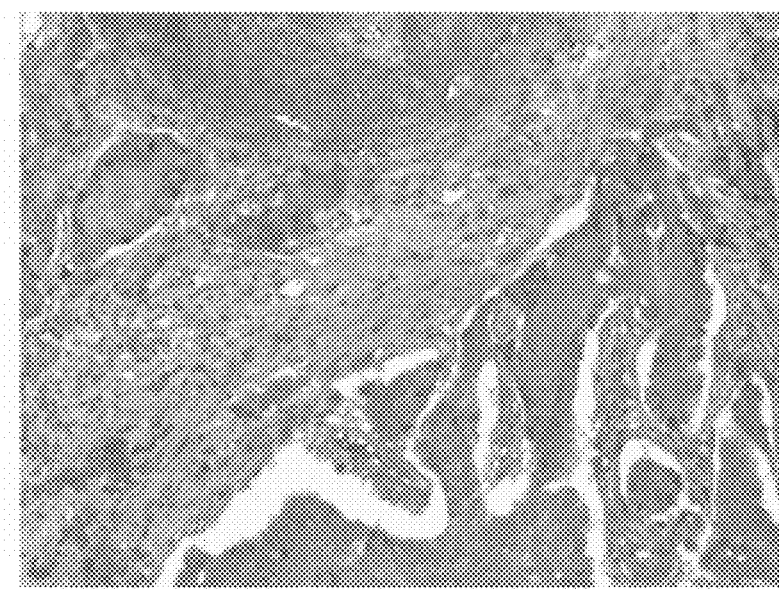
FIG. 12B is a transmitted-light image of a sample prepared with DAPI and an IF label based on a fluorochrome stain (ALEXA FLUOR® 594), and further prepared with a conventional eosin protocol of 1% phloxine B for 20 seconds.
Figure 13D:
FIGS. 13D, 13E, and 13F are images that correspond to blue, green, and red fluorescence emission, respectively, from the sample of FIG. 12B.
Figure 13E:
Figure 13F:
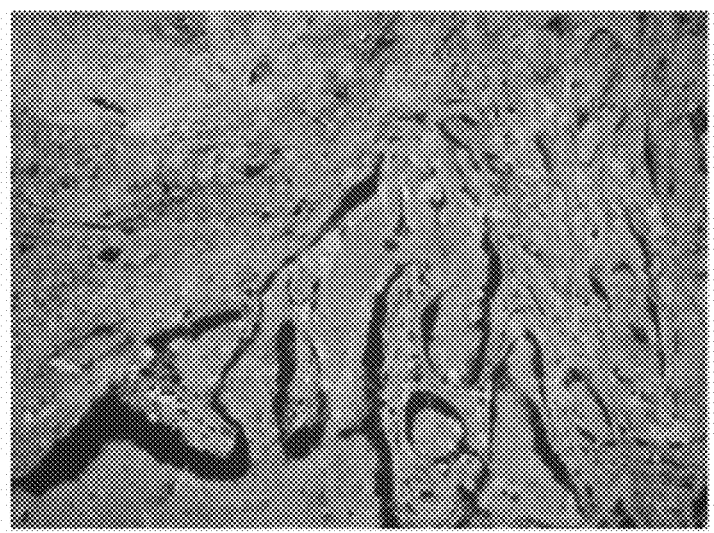

The sample was then subjected to 20 seconds in the working solution of phloxine B, and again imaged in both brightfield and fluorescence modes. At this point, the sample was brightly colored and structures were readily visible by eye when viewed in brightfield. The green component image of the brightfield image is shown as FIG. 12B. Then, a fluorescent image cube was obtained, and its blue, green, and red planes are shown as FIGS. 13D, 13E, and 13F.

Figure 14A:
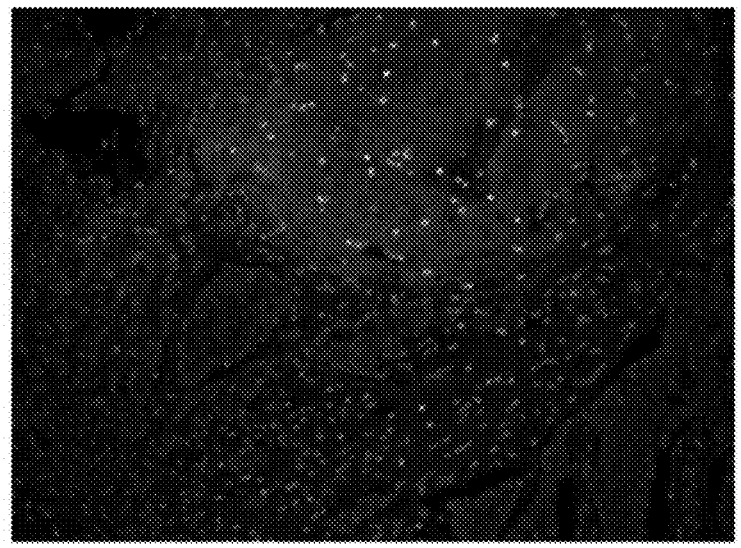
FIGS. 14A and 14B are images of the Her2 and DAPI component signals, respectively, obtained by unmixing a multispectral fluorescence image of the sample of FIG. 12A.
Figure 14B:
Figure 15A:
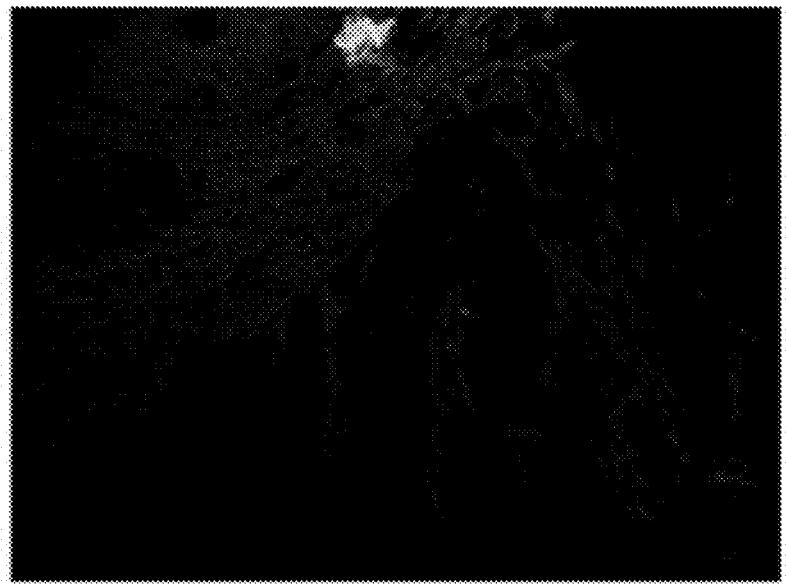
FIGS. 15A and 15B are images of the Her2 and DAPI component signals, respectively, obtained by unmixing a multispectral fluorescence image of the sample of FIG. 12B.
Figure 15B:
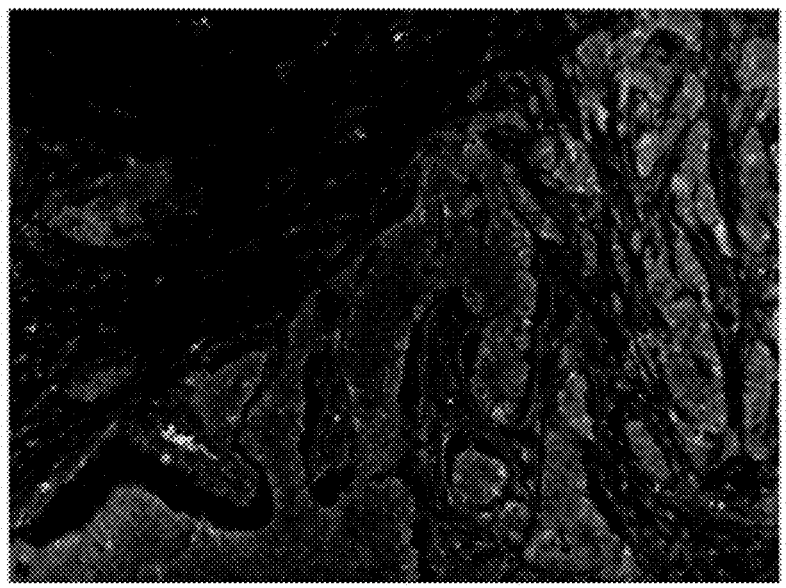

These image cubes were unmixed using the same spectral curves for DAPI and for the fluorochrome stain (ALEXA FLUOR® 594) as in the first experiment. The phloxine B spectrum was obtained by sampling a bright region of the fluorescent image cube taken after the sample had been subjected to the working solution. Using these spectra, component images were obtained for DAPI, phloxine B, tissue, and the Her2 compounds. FIGS. 14A and 14B show the Her2 and DAPI component images for the sample after it was exposed to 1:50 dilution of phloxine B, and these show good delineation of the nuclei and of the Her2 regions. In contrast, the Her2 and DAPI component images in FIGS. 15A and 15B obtained from fluorescence imaging of the sample after it was exposed to working solution of phloxine B are of poorer quality. There are no nuclei visible in the DAPI image, for example, although this stain is conventionally used to visualize nuclei.

Figure 16A:
FIGS. 16A, 16B, and 16C are images that correspond to the blue, green, and red channels, respectively, of a synthetic transmitted-light H&E image of the sample of FIG. 12A, where a full multi-spectral image cube was acquired and then spectrally unmixed to produce estimates of the DAPI, eosin (phloxine B), and fluorochrome stain (ALEXA FLUOR® 594) contributions at each pixel, and the synthetic transmitted-light H&E image was produced by rendering the DAPI signal in blue and the eosin (phloxine B) signal in pink against a white background.
Figure 16B:
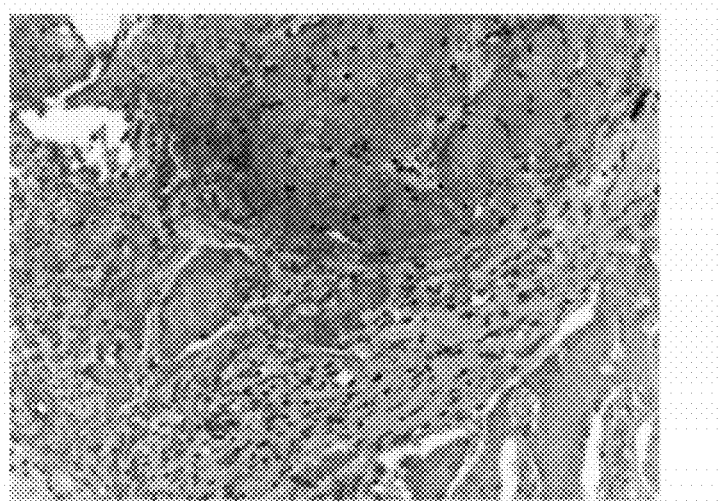
Figure 16C:
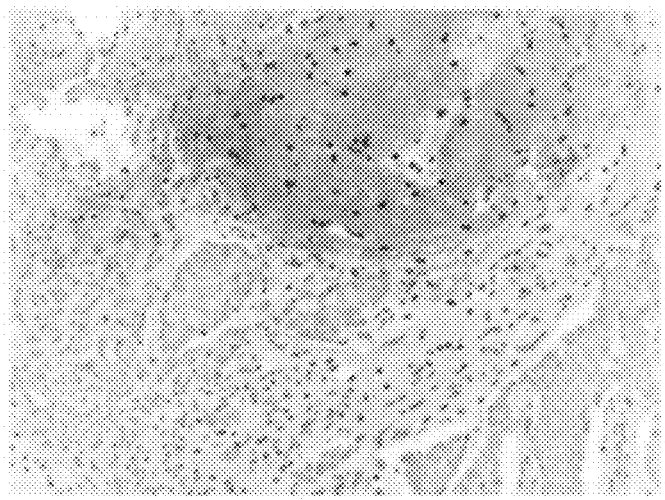
Figure 17A:
FIGS. 17A, 17B, and 17C are images that correspond to the blue, green, and red channels, respectively, of a synthetic transmitted-light H&E image of the sample of FIG. 12B, where a full multi-spectral image cube was acquired and then spectrally unmixed to produce estimates of the DAPI, eosin (phloxine B), and fluorochrome stain (ALEXA FLUOR® 594) contributions at each pixel, and the synthetic transmitted-light H&E image was produced by rendering the DAPI signal in blue and the eosin (phloxine B) signal in pink stain against a white background.
Figure 17B:
Figure 17C:
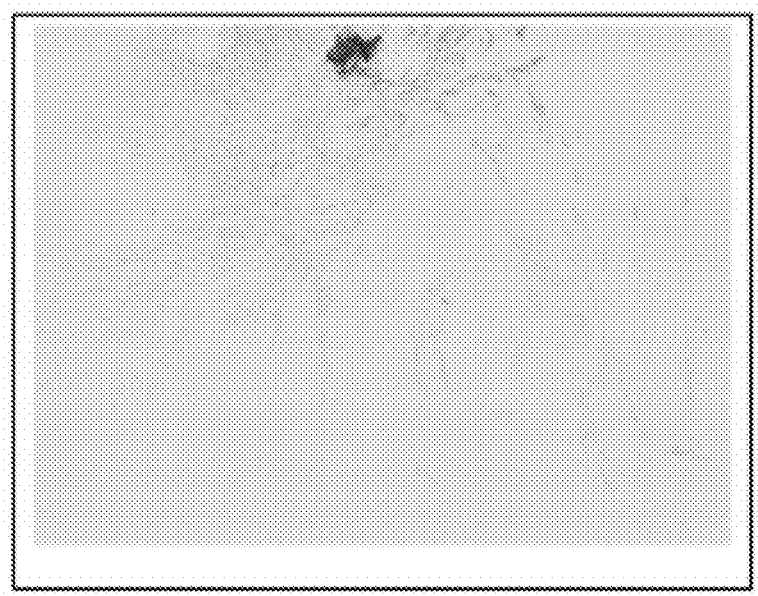
Figure 22:
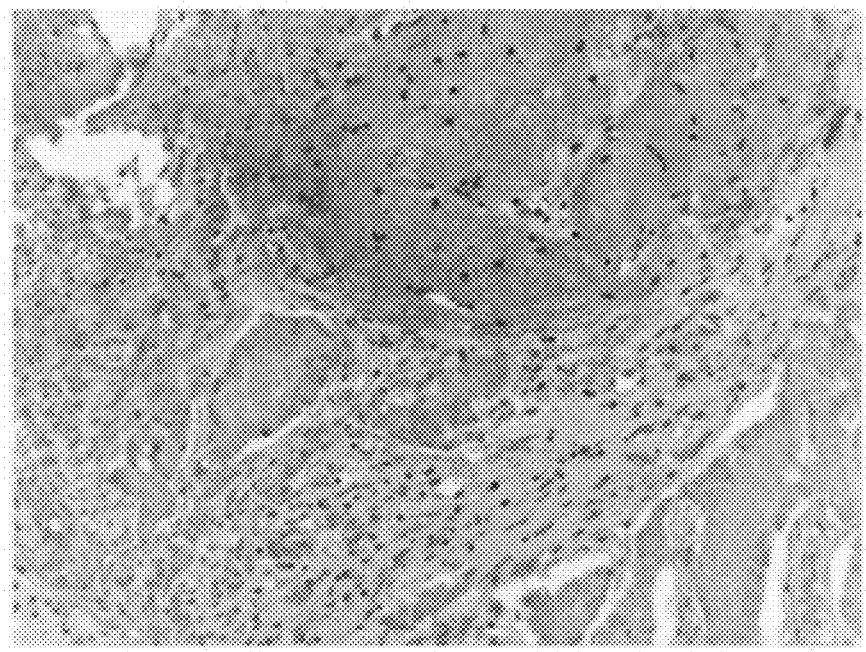
FIG. 22 shows an image that corresponds to the combined images of FIGS. 16A-C.
Figure 23:
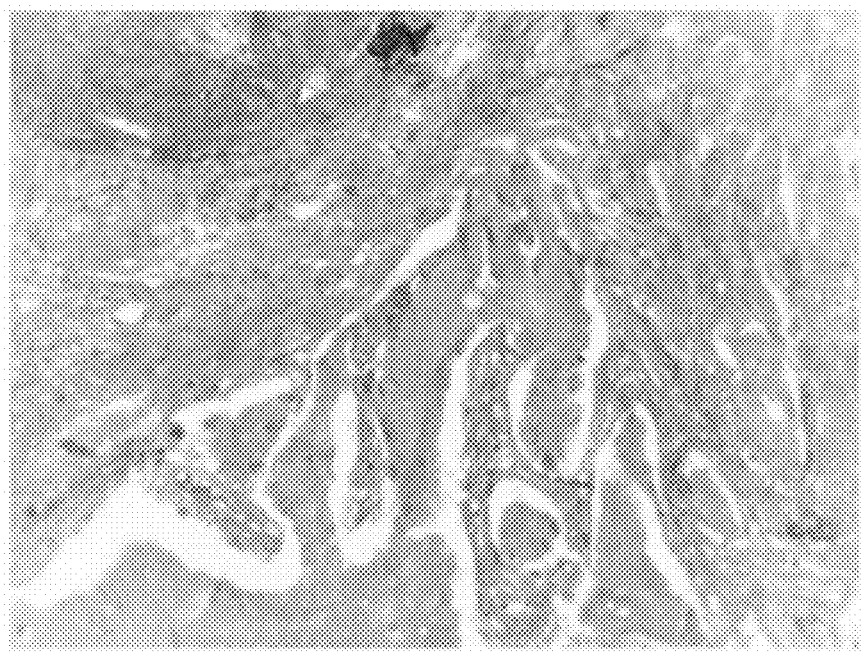
FIG. 23 shows an image that corresponds to the combined images of FIGS. 17A-C.

Synthetic brightfield H&E views were generated using the Nuance software, with DAPI mapped to a blue color, and eosin mapped to a pink color. The individual blue, green, and red color planes are shown as FIGS. 16A, 16B, and 16C, and an image that corresponds to a combination of the three images of FIGS. 16A-16C is shown in FIG. 22. The synthetic view obtained from the sample after 1:50 dilution is very similar to views of similar samples when processed with conventional protocols and viewed in brightfield imaging mode. A synthetic brightfield H&E view was also generated for the sample after exposure to the working phloxine B solution, and individual blue, green, and red color planes of this view are shown as FIGS. 17A, 17B, and 17C, and FIG. 23 shows an image that corresponds to a combination of the images of FIGS. 17A-17C. In contrast to the images of FIGS. 16A-C, the images in FIGS. 17A-C do not bear a close resemblance to a true brightfield H&E view.

Overall, the results of the third experiments were similar to the results obtained using the mixture of eosin Y and phloxine B in the first experiment.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A method for imaging a biological sample, the method comprising:
   a. staining the sample with a first stain comprising eosin and at least one additional stain;
   b. directing excitation light to the sample to cause each of the stains to emit fluorescence; and
   c. recording images of the fluorescence emitted from the stains in the sample,
   wherein the amount of eosin in the sample is sufficiently dilute to cause the sample to have an average optical density of less than 0.10 at green wavelengths.

2. The method of claim 1, wherein the amount of eosin in the sample is sufficiently dilute to cause the sample to have an average optical density of less than 0.05 at green wavelengths.

3. The method of claim 1, wherein the staining of the sample with the first stain comprising eosin comprises contacting the sample for one second or less with a solution having an eosin concentration of 0.01 g or less of eosin per 100 mL of solution.

4. The method of claim 1, wherein the amount of eosin in the sample is sufficient to produce detectable fluorescence by the eosin in response to the excitation light.

5. The method of claim 1, wherein the green wavelengths are 530 nm through 570 nm.

6. The method of claim 1, wherein the eosin comprises at least one of eosin Y, eosin B, and phloxine.

7. The method of claim 1, wherein the recorded images are spectrally resolved into different spectral bands.

8. The method of claim 7, wherein at least some of the spectral bands correspond to a fluorescence wavelength range for a respective one of the stains.

9. The method of claim 1, wherein the biological sample comprises blood, cells, or tissue sections.

10. The method of claim 1, wherein the at least one additional stain comprises a fluorescent nuclear counterstain.

11. The method of claim 10, wherein the fluorescent counterstain comprises DAPI or Hoechst.

12. The method of claim 10, wherein the at least one additional stain further comprises at least one immunofluorescent stain.

13. The method of claim 12, wherein the immunofluorescent stain comprises quantum dots.

14. The method of claim 1, wherein the directing of the excitation light comprises sequentially directing excitation light in different spectral bands to the sample.

15. The method of claim 1, wherein the recording of the fluorescence comprises recording images of the fluorescence in each of multiple different spectral bands.

16. The method of claim 1, further comprising computationally processing the recorded images to obtain information about the sample.

17. The method of claim 16, wherein the processing of the recorded images comprises spectrally unmixing the recorded images into unmixed images, wherein each unmixed image corresponds to fluorescence from a respective one of the stains.

18. The method of claim 16, wherein the processing of the recorded images comprises generating a bright-field image of the sample from the recorded fluorescence images.

19. The method of claim 18, wherein the bright-field image comprises pink regions corresponding regions of the sample that localize eosin and blue regions corresponding to regions of the sample containing nuclei.

20. The method of claim 19, wherein the bright-field image further comprises additional regions rendered to correspond to regions of the sample that localize an immunofluorescent stain.

21. The method of claim 16, further comprising outputting the information about the sample.

22. The method of claim 21, wherein the outputted information comprises a synthetic image derived from the recorded images.

23. The method of claim 1, wherein a difference between the average optical density of the sample at the green wavelengths and an average optical density of the sample at red wavelengths is 0.08 or less.

24. The method of claim 1, wherein the red wavelengths are 610 nm through 650 nm.

25. The method of claim 1, wherein the contribution of the eosin to the average optical density of the sample is less than 0.05.

26. A method for imaging a biological sample, the method comprising:
   a. staining the sample with a first stain comprising eosin, a nuclear counterstain, and at least one immunofluorescent stain, wherein the amount of eosin in the sample is sufficiently dilute to cause the sample to have an average optical density of less than 0.10 at green wavelengths;
   b. directing excitation light to the sample to cause each of the stains to emit fluorescence, wherein the amount of eosin in the sample is sufficient to produce detectable fluorescence by the eosin in response to the excitation light;
   c. recording images of the fluorescence emitted from the stains in the sample;
   d. computationally processing the recorded images to produce a synthetic image; and
   e. displaying the synthetic image.

27. The method of claim 26, wherein the synthetic image comprises a bright-field image comprising pink regions corresponding regions of the sample that localize eosin, blue regions corresponding to regions of the sample containing nuclei, and additional regions rendered to correspond to regions of the sample that localize the immunofluorescent stain.

28. The method of claim 26, wherein the processing of the recorded images comprises spectrally unmixing the recorded images into unmixed images, and wherein each unmixed image corresponds to fluorescence from a respective one of the stains.

29. The method of claim 26, wherein the biological sample comprises blood.

30. The method of claim 26, wherein the eosin in the sample has an average optical density of less than 0.05 at wavelengths between 530 nm and 580 nm.

31. The method of claim 26, wherein a difference between the average optical density of the sample in the green wavelengths and an average optical density of the sample at red wavelengths is 0.08 or less.

32. The method of claim 26, wherein the red wavelengths are 610 nm through 650 nm.

33. The method of claim 26, wherein the contribution of the eosin to the average optical density of the sample is less than 0.05.

34. A method for imaging a biological sample, the method comprising:
   a. staining the sample with a first stain comprising eosin and at least one additional stain;

b. measuring fluorescence emission from eosin and from the at least one additional stain in the sample; and
c. spectrally unmixing the measured fluorescence emission into contributions from eosin and from the at least one additional stain,
wherein the amount of eosin in the sample is sufficiently dilute to cause the sample to have an average optical density of less than 0.10 at green wavelengths.

* * * * *